US012588846B2

(12) United States Patent
Carmel et al.

(10) Patent No.: US 12,588,846 B2
(45) Date of Patent: Mar. 31, 2026

(54) METHODS, SYSTEMS, AND DEVICES FOR DETERMINING A STATUS OF BRAIN AND/OR NERVE FUNCTIONS OF A PATIENT

(71) Applicant: HADASIT MEDICAL RESEARCH SERVICES & DEVELOPMENT LTD., Jerusalem (IL)

(72) Inventors: Ilan Carmel, Tel Mond (IL); Yousef Farraj, Rama Village (IL); Jose Cohen, Jerusalem (IL)

(73) Assignee: HADASIT MEDICAL RESEARCH SERVICES & DEVELOPMENT LTD., Jerusalem (IL)

( * ) Notice: Subject to any disclaimer, the term of this patent is extended or adjusted under 35 U.S.C. 154(b) by 0 days.

(21) Appl. No.: 18/689,416

(22) PCT Filed: Aug. 16, 2022

(86) PCT No.: PCT/IL2022/050890
§ 371 (c)(1),
(2) Date: Mar. 5, 2024

(87) PCT Pub. No.: WO2023/021509
PCT Pub. Date: Feb. 23, 2023

(65) Prior Publication Data
US 2024/0324924 A1     Oct. 3, 2024

Related U.S. Application Data

(60) Provisional application No. 63/233,863, filed on Aug. 17, 2021.

(51) Int. Cl.
*A61B 5/16*          (2006.01)
*A61B 3/11*          (2006.01)
(Continued)

(52) U.S. Cl.
CPC .............. *A61B 5/163* (2017.08); *A61B 5/162* (2013.01); *A61B 5/4064* (2013.01)

(58) Field of Classification Search
CPC ....... A61B 5/163; A61B 5/162; A61B 5/4064; A61B 5/0082; A61B 5/0075;
(Continued)

(56) References Cited

U.S. PATENT DOCUMENTS 4,007,980 A     2/1977  Bracher et al.
5,777,719 A     7/1998  Williams et al.
(Continued)

FOREIGN PATENT DOCUMENTS

JP          H11130623  A      5/1999
JP           3137375  U     10/2007
(Continued)

OTHER PUBLICATIONS

PCT International Search Report for International Application No. PCT/IL2022/050890, mailed Nov. 22, 2022, 7pp.
(Continued)

*Primary Examiner* — Boniface N Nganga
(74) *Attorney, Agent, or Firm* — The Roy Gross Law Firm, LLC; Roy D. Gross

(57) ABSTRACT

A system, device, and methods configured for determining a status of brain and/or nerve functions of a patient having closed eyelids, comprising obtaining a plurality of consecutive frames which captures light transmitted through the closed eyelid of the patient and analyzing the gray level of pixels within frames of the plurality of consecutive frames such as to track the location of the pupil, calculate the size of the pupil, and/or monitor a pupillary reflex, and determining a status of brain and/or nerve functions of the patient based, at least in part, on the analysis.

17 Claims, 11 Drawing Sheets

(51) Int. Cl.
  *A61B 3/14* (2006.01)
  *A61B 5/00* (2006.01)
(58) Field of Classification Search
  CPC ... A61B 5/4821; A61B 5/6803; A61B 5/0077;
        A61B 3/14; A61B 3/112; A61B 3/113
  USPC ........................................................ 351/210
  See application file for complete search history.

(56) References Cited

U.S. PATENT DOCUMENTS

| | | | |
|---|---|---|---|
| 6,126,607 A | 10/2000 | Whitmore, III et al. | |
| 6,528,993 B1* | 3/2003 | Shin ..................... | G01R 33/032 |
| | | | 359/489.08 |
| 6,669,651 B1 | 12/2003 | Fukushima et al. | |
| 11,122,972 B2 | 9/2021 | Cohen et al. | |
| 2005/0159775 A1 | 7/2005 | Reynolds | |
| 2006/0013844 A1 | 1/2006 | Meriaux | |
| 2006/0115519 A1 | 6/2006 | Matsui | |
| 2009/0312817 A1 | 12/2009 | Hogle et al. | |
| 2010/0018542 A1 | 1/2010 | Konrad | |
| 2011/0077548 A1 | 3/2011 | Torch | |
| 2012/0268715 A1* | 10/2012 | Stark ..................... | A61B 5/163 |
| | | | 351/205 |
| 2012/0293773 A1 | 11/2012 | Publicover et al. | |
| 2014/0185010 A1 | 7/2014 | Bernert et al. | |
| 2014/0340287 A1 | 11/2014 | Achilefu et al. | |
| 2014/0343432 A1 | 11/2014 | Humayun | |
| 2015/0245766 A1 | 9/2015 | Rennaker et al. | |
| 2016/0066820 A1 | 3/2016 | Sales et al. | |
| 2016/0073874 A1 | 3/2016 | Tsai et al. | |
| 2016/0270656 A1 | 9/2016 | Samec et al. | |
| 2017/0115742 A1 | 4/2017 | Xing et al. | |
| 2017/0311799 A1* | 11/2017 | Holt ..................... | A61B 3/152 |
| 2018/0235498 A1 | 8/2018 | Whang et al. | |
| 2019/0282086 A1 | 9/2019 | Cohen et al. | |
| 2020/0329849 A1 | 10/2020 | Freer et al. | |

FOREIGN PATENT DOCUMENTS

| | | | |
|---|---|---|---|
| JP | 2007-531579 A | 11/2007 | |
| JP | 2008-543352 A | 12/2008 | |
| JP | 2010-017205 A | 1/2010 | |
| JP | 2011-508651 A | 3/2011 | |
| JP | 2013-248312 A | 12/2013 | |
| JP | 2013-248313 A | 12/2013 | |
| KR | 200199749 Y1 | 11/2000 | |
| WO | 2007104870 A2 | 9/2007 | |
| WO | 2018093292 A1 | 5/2018 | |

OTHER PUBLICATIONS

PCT Written Opinion for International Application No. PCT/IL2022/050890, mailed Nov. 22, 2022, 6pp.

Almohimeed, et al., Development of wearable and flexible ultrasonic sensor for skeletal muscle monitoring, Joint UFFC, EFTC and PFM Symposium, 2013, pp. 1137-1140. Retrieved Oct. 8, 2021; doi: 10.1109/ULTSYM.2013.0291.

Zhou et al., Pupil ultrasound images segmentation and diameter measurements based on improved graph cuts, Chinese Journal of Biomedical Engineering, 2015, vol. 34, No. 4, pp. 399-406; Retrieved Oct. 8, 2021.

Sonivate Medical, "SonicEye Dual-Plane Ultrasound Probe—Specifcations" downloaded on Feb. 21, 2019 from: [http://sonivate.com/products/soniceye/]. Retrieved Oct. 8, 2021.

Ultrasound Schools Info: Diagnostic Medical Sonography Career & Education Guide, "The next wave in ultrasound technology", downloaded on Feb. 21, 2019 from: [http://www.ultrasoundschoolsinfo.com/next-wave-ultrasound-technology]; Retrieved Oct. 8, 2021.

Lewis, Jr., George K. , "Miniaturizing a wearable ultrasound pain therapy device" (2014), Dowloaded on Feb. 21, 2019 from: [http://www.medicaldesignbriefs.com/component/content/article/mdb/features/19673]; Retrieved Oct. 8, 2021.

Harries et al. (2010) Ultrasound assessment of extraocular movements and pupillary light reflex in ocular trauma, Amn J of Emergency Medicine, vol. 28, No. 8, pp. 956-959; Retrieved Oct. 8, 2021; doi:10.1016/j.ajem.2009.06.026.

PCT International Search Report for International Application No. PCT/IL2017/050668, mailed Sep. 28, 2017, 5pp. 5 pages.

PCT Written Opinion for International Application No. PCT/IL2017/050668, mailed Sep. 28, 2017, 5pp. 5 pages.

Kobashi et al. (2008). Eye Position Estimation During Sleep Using Infrared Video in Functional MRI. JACIII. 12. 32-40. 10.20965/jaciii.2008.p0032.

* cited by examiner

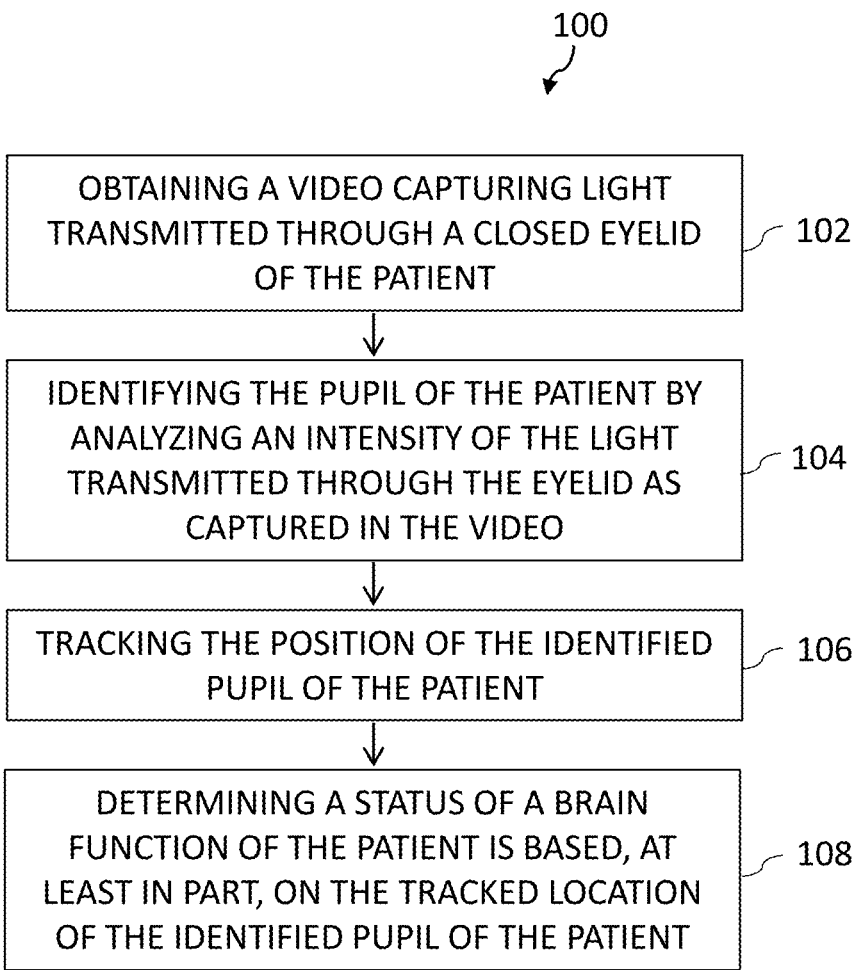

100

OBTAINING A VIDEO CAPTURING LIGHT
TRANSMITTED THROUGH A CLOSED EYELID
OF THE PATIENT — 102

IDENTIFYING THE PUPIL OF THE PATIENT BY
ANALYZING AN INTENSITY OF THE LIGHT
TRANSMITTED THROUGH THE EYELID AS
CAPTURED IN THE VIDEO — 104

TRACKING THE POSITION OF THE IDENTIFIED
PUPIL OF THE PATIENT — 106

DETERMINING A STATUS OF A BRAIN
FUNCTION OF THE PATIENT IS BASED, AT
LEAST IN PART, ON THE TRACKED LOCATION
OF THE IDENTIFIED PUPIL OF THE PATIENT — 108

FIG. 1

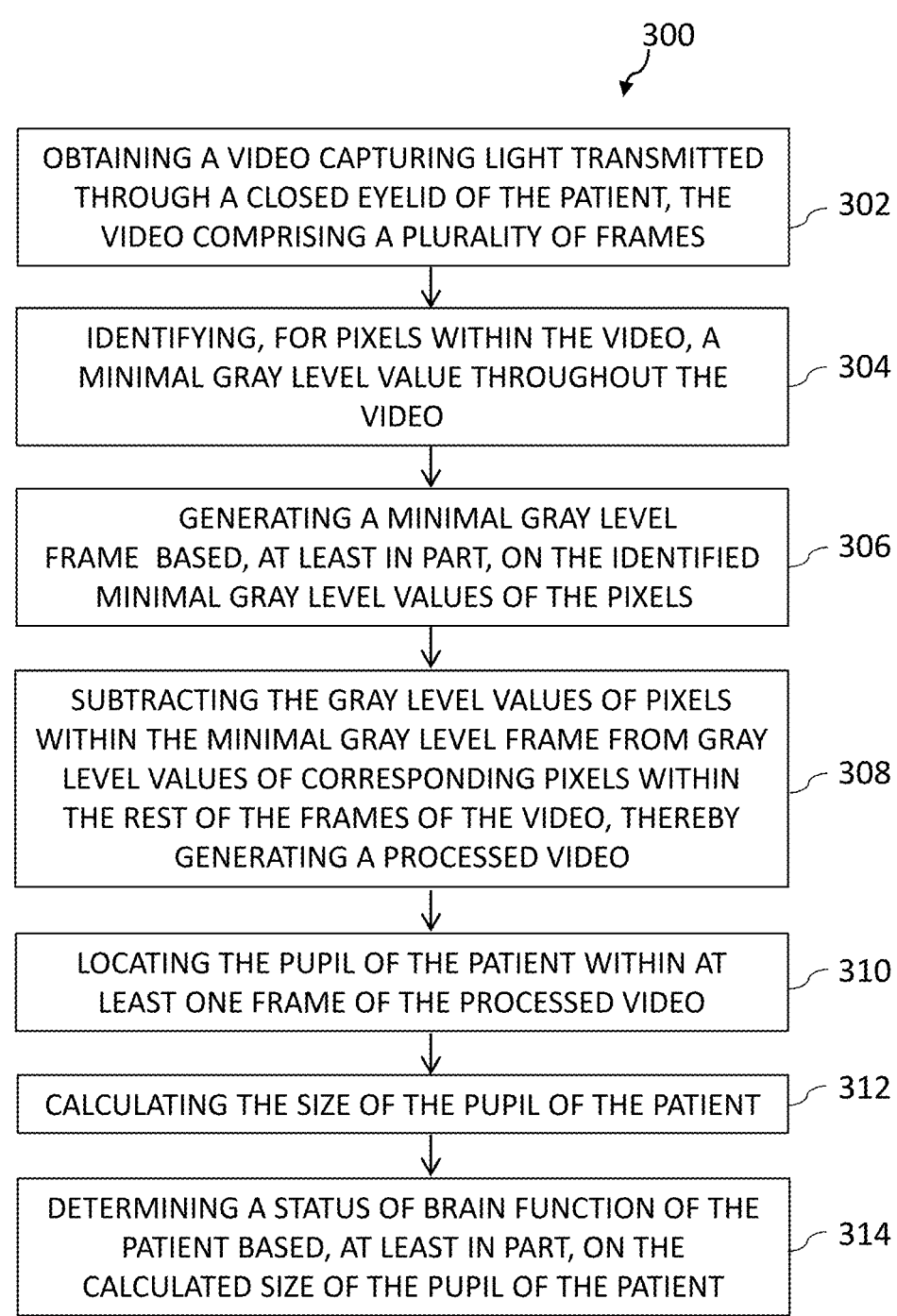

300

OBTAINING A VIDEO CAPTURING LIGHT TRANSMITTED
THROUGH A CLOSED EYELID OF THE PATIENT, THE
VIDEO COMPRISING A PLURALITY OF FRAMES
— 302

IDENTIFYING, FOR PIXELS WITHIN THE VIDEO, A
MINIMAL GRAY LEVEL VALUE THROUGHOUT THE
VIDEO
— 304

GENERATING A MINIMAL GRAY LEVEL
FRAME BASED, AT LEAST IN PART, ON THE IDENTIFIED
MINIMAL GRAY LEVEL VALUES OF THE PIXELS
— 306

SUBTRACTING THE GRAY LEVEL VALUES OF PIXELS
WITHIN THE MINIMAL GRAY LEVEL FRAME FROM GRAY
LEVEL VALUES OF CORRESPONDING PIXELS WITHIN
THE REST OF THE FRAMES OF THE VIDEO, THEREBY
GENERATING A PROCESSED VIDEO
— 308

LOCATING THE PUPIL OF THE PATIENT WITHIN AT
LEAST ONE FRAME OF THE PROCESSED VIDEO
— 310

CALCULATING THE SIZE OF THE PUPIL OF THE PATIENT
— 312

DETERMINING A STATUS OF BRAIN FUNCTION OF THE
PATIENT BASED, AT LEAST IN PART, ON THE
CALCULATED SIZE OF THE PUPIL OF THE PATIENT
— 314

FIG. 3

METHODS, SYSTEMS, AND DEVICES FOR DETERMINING A STATUS OF BRAIN AND/OR NERVE FUNCTIONS OF A PATIENT

TECHNICAL FIELD

The present disclosure relates generally to the field of pupil size and/or movement assessment and usage thereof in determining a status of brain and/or nerve functions of a patient.

BACKGROUND

Frequent pupil evaluation is part of the protocol for care of critically injured or ill patients.

Currently, most pupil measurements are conducted by visual observation performed by nursing staff. The patients' eyelids are lifted open and pupillary size and light reactivity (also referred to herein as pupillary reflex) are estimated by visual observation or at best by measuring using a ruler, and pupils' reactivity is assessed using a penlight.

However, such manual pupillary assessment is subject to inaccuracies and inconsistencies and is characterized by large inter-examiner variability. Moreover, ambient light conditions can affect the validity of the visual assessment of the pupil and increase the inter-observer disagreement. These factors may include, for example, poor lighting conditions in the patient's room, the examiner's visual acuity, as well as his/hers distance and orientation with respect to the patient's eye.

Moreover, the manual evaluation requires the nurse to attend to the patient, thus making it a time consuming, labor-intensive assessment, which most often is only performed at routine visits hours apart. As a result, a change in pupil size is seldom detected as it occurs, despite the fact that immediate medical intervention is critical to patient survival and neurological outcome.

The manual evaluation also requires frequent visits to the patient, which may also be time consuming and labor intensive. The evaluation as described can only monitor difference in the eyes of the patient between different visits of the nurse, thereby abnormal movement of the pupil goes undetected. There is, therefore, a need for devices and methods enabling objective, and intermittent or continuous evaluation of a patient's pupil size and/or pupillary reflex, as well as the tracking of the location and movement of the pupil.

SUMMARY

Aspects of the disclosure, according to some embodiments thereof, relate to systems, devices, and methods for examination of a pupil of a patient having closed eyelids. According to some embodiments, the systems, devices, and methods disclosed herein are configured to examine the pupil of the patient by analyzing one or more frames capturing light transmitted from the vitreous and through the eyelid of the patient. According to some embodiments, the systems, devices, and methods disclosed herein are configured to detect and/or classify a brain function and/or nerve function of the patient based, at least in part, on the analyzed frames.

Advantageously, the systems, devices, and methods disclosed herein enable continuous monitoring of the brain function and/or nerve function of the patient. According to some embodiments, the monitoring of the brain function and/or nerve function of the patient may be in real time.

According to some embodiments, the monitoring may implement a device which may be operated by a processing module, and thereby does not require user assistance. Advantageously, systems, devices, and methods disclosed herein enable continuous monitoring of the brain function and/or nerve function of the patient without a nurse or operator.

Advantageously, the systems, devices, and methods disclosed herein enable continuous monitoring of the brain function and/or nerve function of the patient while the eyelids of the patient are closed. Monitoring of the brain function and/or nerve function of the patient while the eyelids of the patient are closed therefore enables monitoring of the pupils of the patient without drying of the eyes. According to some embodiments, the systems, devices, and methods disclosed herein enable monitoring of brain function and/or nerve function of a patient that may be in a sedated state, asleep, or a coma.

According to some embodiments, the systems, devices, and methods disclosed herein enable continuous monitoring of the brain function and/or nerve function of the patient by acquiring and/or analyzing gray level values of pixels within the captured frames. According to some embodiments, the systems, devices, and methods disclosed herein may be configured to take into account varying skin thickness of the eyelid, such as caused by skin overlaps. According to some embodiments, the systems, devices, and methods disclosed herein may be configured to analyze and/or acquire the size, location, gray level values, and/or movement of the pupil while taking into account images which depict only portions of the pupil.

According to some embodiments, the systems, devices, and methods disclosed herein may be configured to calculate and/or acquire the location, size, gray level values, shape, movements, and/or modifications of the identified pupil by analyzing the gray level values within the captured frames. According to some embodiments, the systems, devices, and methods disclosed herein may be configured to implement algorithms, such as one or more machine learning algorithms, configured to calculate the location, size, shape, movements, and modifications of the identified pupil. According to some embodiments, the algorithm may be configured to account for varying gray levels caused by different pupil sizes. According to some embodiments, the algorithm may be configured to account for varying gray levels caused by different pupil location in relation to a light source and/or image capturing module.

According to some embodiments there is provided a method for determining a status of brain and/or nerve functions of a patient, the method including: obtaining a plurality of consecutive frames capturing light transmitted through a closed eyelid of the patient, identifying the pupil of the patient by analyzing an intensity of the light transmitted through the eyelid as captured in the plurality of consecutive frames, tracking the location of the identified pupil of the patient in at least a portion of the plurality of consecutive frames, and determining a status of brain and/or nerve functions of the patient is based, at least in part, on the tracked location of the identified pupil of the patient.

According to some embodiments there is provided a method for determining a status of brain and/or nerve functions of a patient, the method including: obtaining a plurality of consecutive frames capturing light transmitted through a closed eyelid of the patient, identifying, for pixels within the plurality of consecutive frames, a minimal gray level value throughout the plurality of consecutive frames, generating a minimal gray level frame based, at least in part, on the identified minimal gray level values of the pixels, and subtracting the gray level values of pixels within the minimal gray level frame from gray level values of corresponding pixels within the rest of the frames of the plurality of consecutive frames, thereby generating a processed plurality of consecutive frames, locating the pupil of the patient within at least one frame of the processed plurality of consecutive frames, calculating the size of the pupil of the patient, and determining a status of brain and/or nerve functions of the patient based, at least in part, on the calculated size of the pupil of the patient.

According to some embodiments there is provided a method for determining a status of brain and/or nerve functions of a patient in an emergency setting or ambulance, the method including: obtaining a plurality of consecutive frames capturing light transmitted through a closed eyelid of the patient, identifying the pupil of the patient by analyzing an intensity of the light transmitted through the eyelid as captured in the plurality of consecutive frames, tracking the location of the identified pupil of the patient in at least a portion of the plurality of consecutive frames, and determining a status of brain and/or nerve functions of the patient is based, at least in part, on the tracked location of the identified pupil of the patient.

According to some embodiments there is provided a method for determining a status of brain and/or nerve functions of a patient in an emergency setting or ambulance, the method including: obtaining a plurality of consecutive frames capturing light transmitted through a closed eyelid of the patient, identifying, for pixels within the plurality of consecutive frames, a minimal gray level value throughout the plurality of consecutive frames, generating a minimal gray level frame based, at least in part, on the identified minimal gray level values of the pixels, and subtracting the gray level values of pixels within the minimal gray level frame from gray level values of corresponding pixels within the rest of the frames of the plurality of consecutive frames, thereby generating a processed plurality of consecutive frames, locating the pupil of the patient within at least one frame of the processed plurality of consecutive frames, calculating the size of the pupil of the patient, and determining a status of brain and/or nerve functions of the patient based, at least in part, on the calculated size of the pupil of the patient.

According to some embodiments there is provided a method for determining a status of brain and/or nerve functions of a patient in a sleep disorder lab setting, the method including: obtaining a plurality of consecutive frames capturing light transmitted through a closed eyelid of the patient, identifying, for pixels within the plurality of consecutive frames, a minimal gray level value throughout the plurality of consecutive frames, generating a minimal gray level frame based, at least in part, on the identified minimal gray level values of the pixels, and subtracting the gray level values of pixels within the minimal gray level frame from gray level values of corresponding pixels within the rest of the frames of the plurality of consecutive frames, thereby generating a processed plurality of consecutive frames, locating the pupil of the patient within at least one frame of the processed plurality of consecutive frames, calculating the size of the pupil of the patient, and determining a status of brain and/or nerve functions of the patient based, at least in part, on the calculated size of the pupil of the patient.

According to some embodiments, the method further includes light toward a vitreous cavity of the patient using one or more light sources and wherein the light captured in the plurality of consecutive frames is the light emitted by the one or more light sources.

According to some embodiments, the identifying of the pupil of the patient is in real time.

According to some embodiments, the tracking of the position of the pupil is in real time.

According to some embodiments, the method further includes contouring at least one segment having a plurality of pixels with a high gray level in at least one frame within the plurality of consecutive frames.

According to some embodiments, the high gray level includes a value of gray level above a predetermined maximum threshold.

According to some embodiments, the method further includes determining a shape of the at least one segment, and wherein identifying of the pupil of the patient is based, at least in part, on the shape of the at least one segment.

According to some embodiments, the method further includes determining a gray level distribution within the at least one segment, and wherein identifying of the pupil of the patient is based, at least in part, on the gray level distribution within the at least one segment.

According to some embodiments, the method further includes determining a maximal gray level value within the at least one segment, and wherein identifying of the pupil of the patient is based, at least in part, on the maximal gray level value within the at least one segment.

According to some embodiments, the method further includes identifying at least one segment having a plurality of pixels with a high gray level within each of at least two frames within the plurality of consecutive frames.

According to some embodiments, the method further includes comparing between at least two identified segments associated with different frames within the plurality of consecutive frames, wherein identifying of the pupil of the patient is based, at least in part, on the comparison between the at least two identified segments.

According to some embodiments, comparing between the at least two identified segments includes comparing any one or more of the shape and/or gray level distribution of the segments.

According to some embodiments, comparing between the at least two identified segments includes comparing the coordinates of pixels within the segment and/or the coordinated of the shape and/or gray level distribution of pixels within the segments.

According to some embodiments, comparing between the at least two identified segments includes comparing a change in gray level within the segments.

According to some embodiments, the at least two frames are consecutive or semi-consecutive.

According to some embodiments, the method further includes identifying one segment as being associated with a pupil of the patient.

According to some embodiments, tracking the position of the identified pupil of the patient includes tracking a change in coordinates of the pixels within a segment identified as being associated with the pupil of the patient.

According to some embodiments, the method further includes classifying the status of the brain and/or nerve functions of the patient as normal or abnormal, based, at least in part, on the tracked location of the pupil of the patient.

According to some embodiments, the method further includes classifying the type of abnormality of the abnormal status of the brain and/or nerve functions of the patient, wherein the abnormality includes a nystagmus.

According to some embodiments, the method includes indexing a status of pupillary activity and/or the status of brain and/or nerve functions of the patient.

According to some embodiments, the method includes mapping the intensity of the light transmitted through the eyelid of the patient.

According to some embodiments, the nystagmus is congenital, idiopathic, secondary to a pre-existing neurological disorder, drug induced or any combination thereof.

According to some embodiments, the method further includes determining a degree of movement of the pupil of the patient, and wherein the determining of the status of the brain and/or nerve functions of the patient is further based, at least in part, on a degree of movement of the identified pupil of the patient.

According to some embodiments, the determining of the status of the brain and/or nerve functions of the patient is further based, at least in part, on a frequency of the movement of the identified pupil of the patient.

According to some embodiments, the determining of the status of the brain and/or nerve functions of the patient is further based, at least in part, on a duration of an abnormal movement the identified pupil of the patient.

According to some embodiments, the patient is a comatose patient, a sedated patient and/or a patient undergoing surgery.

According to some embodiments, determining the status of the brain includes identifying whether the patient suffers from pain or a sleep disorder.

According to some embodiments, determining the status of the brain includes identifying a level of depth of sedation of the patient.

According to some embodiments, the method further includes generating an alarm if an abnormal brain and/or nerve functions is detected.

According to some embodiments, the method further includes generating an alarm if an abnormal pupil movement is detected.

According to some embodiments, the method further includes identifying the pupil of the patient by analyzing an intensity of the light transmitted through the eyelid as captured in the plurality of consecutive frames.

According to some embodiments, corresponding pixels include at least two pixels having a same coordinates throughout different frames of the plurality of consecutive frames and/or the minimal gray level frame.

According to some embodiments, the locating of the pupil of the patient includes locating the center of the pupil of the patient.

According to some embodiments, the method further includes including tracking the location of the pupil of the patient throughout at least a portion of the plurality of consecutive frames.

According to some embodiments, the method further includes determining a baseline pupil size of the pupil of the patient prior to closing of the eyelid of the patient.

According to some embodiments, the baseline pupil size includes at least one of a large baseline size and a small baseline size of the pupil of the patient.

According to some embodiments, the identifying the pupil of the patient further includes taking into account the baseline pupil size.

According to some embodiments, the determining of the status of brain and/or nerve functions of the patient is further based on the baseline pupil size of the patient.

According to some embodiments, the method further includes calculating the change in the size of the pupil as a function of time.

According to some embodiments, the determining the status of brain and/or nerve functions of the patient is further based on change in size of the pupil as a function of time.

According to some embodiments, the calculating of the size of the pupil of the patient is in real time.

According to some embodiments, the method further includes classifying the status of the brain and/or nerve functions of the patient as normal or abnormal, based, at least in part, on the size of the pupil of the patient.

According to some embodiments, the method further includes classifying the status of the brain and/or nerve functions of the patient as normal or abnormal, based, at least in part, on the change in the size of the pupil of the patient as a function of time.

According to some embodiments, the method further includes classifying the type of abnormality of the abnormal status of the brain and/or nerve functions of the patient, wherein the abnormality includes a nystagmus.

According to some embodiments, the nystagmus is congenital, idiopathic, secondary to a pre-existing neurological disorder, drug induced or any combination thereof.

According to some embodiments, the patient is a comatose patient, a sedated patient and/or a patient undergoing surgery.

According to some embodiments, determining the status of the brain includes identifying whether the patient suffers from pain or a sleep disorder.

According to some embodiments, determining the status of the brain includes identifying a level of depth of sedation of the patient.

According to some embodiments, the method further includes generating an alarm if an abnormal brain and/or nerve functions is detected.

According to some embodiments, the method further includes generating an alarm if any one or more of an abnormal pupil size, an abnormal change in the size of the pupil, an abnormal tracked location of the pupil, an abnormal movement of the pupil movement, and/or an abnormal pupil reflex is detected.

According to some embodiments, the method further includes contouring at least one segment having a plurality of pixels with a high gray level in at least one frame within the plurality of consecutive frames.

According to some embodiments, the high gray level includes a value of gray level above a predetermined maximum threshold.

According to some embodiments, the method further includes determining a shape of the at least one segment, and identifying the pupil of the patient based, at least in part, on the shape of the at least one segment.

According to some embodiments, the method further includes determining a gray level distribution within the at least one segment, and identifying the pupil of the patient based, at least in part, on the gray level distribution within the at least one segment.

According to some embodiments, the method further includes determining a maximal gray level value within the at least one segment, and identifying the pupil of the patient based, at least in part, on the maximal gray level value within the at least one segment.

According to some embodiments, the method further includes identifying at least one segment having a plurality of pixels with a high gray level within each of at least two frames within the plurality of consecutive frames.

According to some embodiments, the method further includes comparing between at least two identified segments associated with different frames within the plurality of consecutive frames, and identifying the pupil of the patient based, at least in part, on the comparison between the at least two identified segments.

According to some embodiments, comparing between the at least two identified segments includes comparing any one or more of the shape and/or gray level distribution of the segments.

According to some embodiments, comparing between the at least two identified segments includes comparing the coordinates of pixels within the segment and/or the coordinated of the shape and/or gray level distribution of pixels within the segments.

According to some embodiments, comparing between the at least two identified segments includes comparing a change in gray level within the segments.

According to some embodiments, the at least two frames are consecutive or semi-consecutive.

According to some embodiments, the method further includes identifying one of the at least one segment as being associated with a pupil of the patient.

According to some embodiments, the method further includes determining the degree of urgency of the medical treatment of the patient based on the status of the patient's brain and/or nerve functions.

According to some embodiments, the method further includes relaying the status of brain and/or nerve functions of the patient to a triage unit or emergency department.

According to some embodiments, there is provided a system for examining a pupil of a patient, including: at least one hardware processor in communication with at least one image capturing device configured to capture a plurality of consecutive frames of a pupil of a patient through a closed eyelid of the patient, a non-transitory computer-readable storage medium having stored thereon program code, the program code executable by the at least one hardware processor to: receive the plurality of consecutive frames of the pupil of the patient, identify the pupil of the patient by analyzing an intensity of the light transmitted through the eyelid as captured in the plurality of consecutive frames, track the location of the identified pupil of the patient in at least a portion of the plurality of consecutive frames, and determine a status of brain and/or nerve functions of the patient is based, at least in part, on the tracked location of the identified pupil of the patient.

According to some embodiments, there is provided a system for examining a pupil of a patient, including: at least one hardware processor in communication with at least one image capturing device configured to capture a plurality of consecutive frames of a pupil of a patient through a closed eyelid of the patient, a non-transitory computer-readable storage medium having stored thereon program code, the program code executable by the at least one hardware processor to: receive the plurality of consecutive frames of the pupil of the patient, identify, for pixels within the plurality of consecutive frames, a minimal gray level value throughout the plurality of consecutive frames, generate a minimal gray level frame based, at least in part, on the identified minimal gray level values of the pixels, and subtract the gray level values of pixels within the minimal gray level frame from gray level values of corresponding pixels within the rest of the frames of the plurality of consecutive frames, thereby generating a processed plurality of consecutive frames, locate the pupil of the patient within at least one frame of the processed plurality of consecutive frames, calculate the size of the pupil of the patient, and determine a status of brain and/or nerve functions of the patient based, at least in part, on the calculated size of the pupil of the patient.

According to some embodiments, the system is configured to track the location of the pupil of the patient in real time.

According to some embodiments, the program code is further executable to calculate the radius of the pupil and/or track the location of the pupil of the patient within the received plurality of consecutive frames.

According to some embodiments, the system is configured for determination of a pupil size and/or pupillary reflex of a patient.

According to some embodiments, the at least one hardware processor and/or the non-transitory computer-readable storage are configured to receive the plurality of consecutive frames in real time.

According to some embodiments there is provided a device for examining a pupil of a patient having closed eyelids, the device including: one or more light sources configured to emit light toward a vitreous cavity of the patient through a temple of the patient, a hood configured to minimize photon escape from the patient's temple, the hood including an opening configured for passage of the emitted light, and one or more light detectors configured to detect an intensity of light exiting the patient's pupils in response to the emitted light.

According to some embodiments, the hood is configured to minimize photon escape from around the eye of the patient.

According to some embodiments, at least a portion of an inner surface of the hood includes a reflective surface configured to redirect photons towards the vitreous cavity.

According to some embodiments, at least a portion of an inner surface of the hood includes a light absorbing material configured to absorb photons scattered back from the temple.

According to some embodiments, the device is configured for determining a pupil size and/or pupillary reflex of a patient having closed eyelids.

According to some embodiments, there is provided a device for examining a pupil of a patient having closed eyelids, the device including: one or more light sources configured to emit light toward a vitreous cavity of the patient through a temple of the patient, a frame configured to be positioned on a head of the patient, and one or more light detectors configured to detect an intensity of light exiting the patient's pupils in response to the emitted light, wherein the one or more light detectors are positioned in a housing attached to the frame, the housing is configured to minimize light entering and exiting around the eye of the patient.

According to some embodiments, there is provided a light emitting assembly for emitting light, the assembly including an outer layer having a contact pad, the contact pad having an adhesive layer configured to be attached to a skin of a patient, and an inner layer having one or more light sources configured to emit light through the skin into a cavity of a body organ/tissue of the patient. According to some embodiments, the one or more light sources of the light emitting assembly configured to emit light through the outer layer and into the cavity.

According to some embodiments, the light emitting assembly may be at least partially disposable.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not drawn to scale. Moreover, two different objects in the same figure may be drawn to different scales. In particular, the scale of some objects may be greatly exaggerated as compared to other objects in the same figure.

In block diagrams and flowcharts, optional elements/components and optional stages may be included within dashed boxes.

In the figures:

FIG. 1 shows a flowchart of functional steps in a method for determining a status of brain and/or nerve functions of a patient, in accordance with some embodiments of the present invention;

FIG. 2A shows a frame from an exemplary plurality of consecutive frames, in accordance with some embodiments of the present invention;

FIG. 2B shows a frame from an exemplary plurality of consecutive frames with identified segmentations, in accordance with some embodiments of the present invention;

FIG. 3 shows a flowchart of functional steps in a method for determining a status of brain and/or nerve functions of a patient, in accordance with some embodiments of the present invention;

FIG. 4A shows a frame from an exemplary plurality of consecutive frames, in accordance with some embodiments of the present invention;

FIG. 4B shows a frame from an exemplary plurality of consecutive frames after having a minimal gray level frame subtracted therefrom, in accordance with some embodiments of the present invention;

FIG. 5 shows a schematic illustration of a system for examining a pupil of a patient having closed eyelids, in accordance with some embodiments of the present invention;

FIG. 6 shows a schematic illustration of a system for examining a pupil of a patient having closed eyelids, in accordance with some embodiments of the present invention;

FIG. 7 shows a schematic illustration of a device for examining a pupil of a patient having closed eyelids, in accordance with some embodiments of the present invention;

FIG. 8 shows a schematic illustration of a device for examining a pupil of a patient having closed eyelids, in accordance with some embodiments of the present disclosure;

FIG. 9 shows a schematic illustration of a perspective side view of a light emitting assembly, in accordance with some embodiments of the present invention;

Figure 10A:
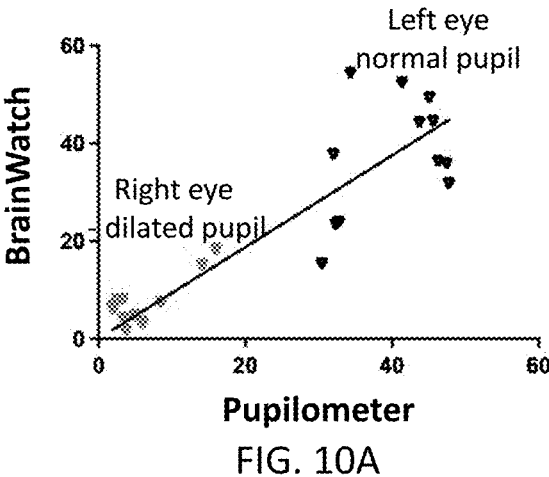
Figure 10B:
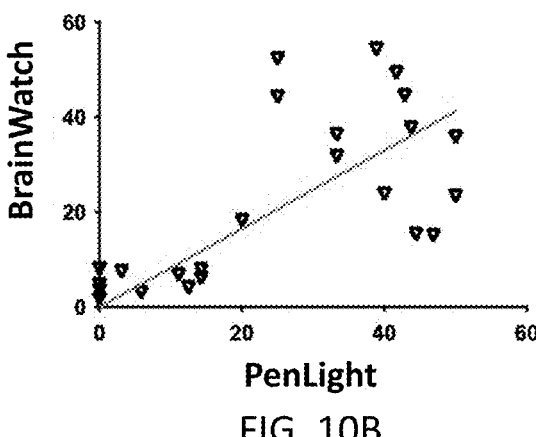
Figure 10C:
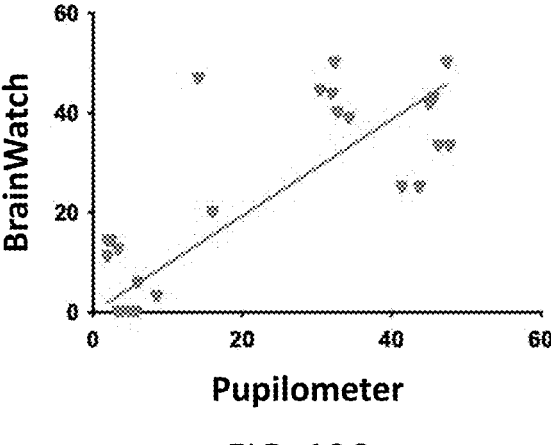
Figure 11:
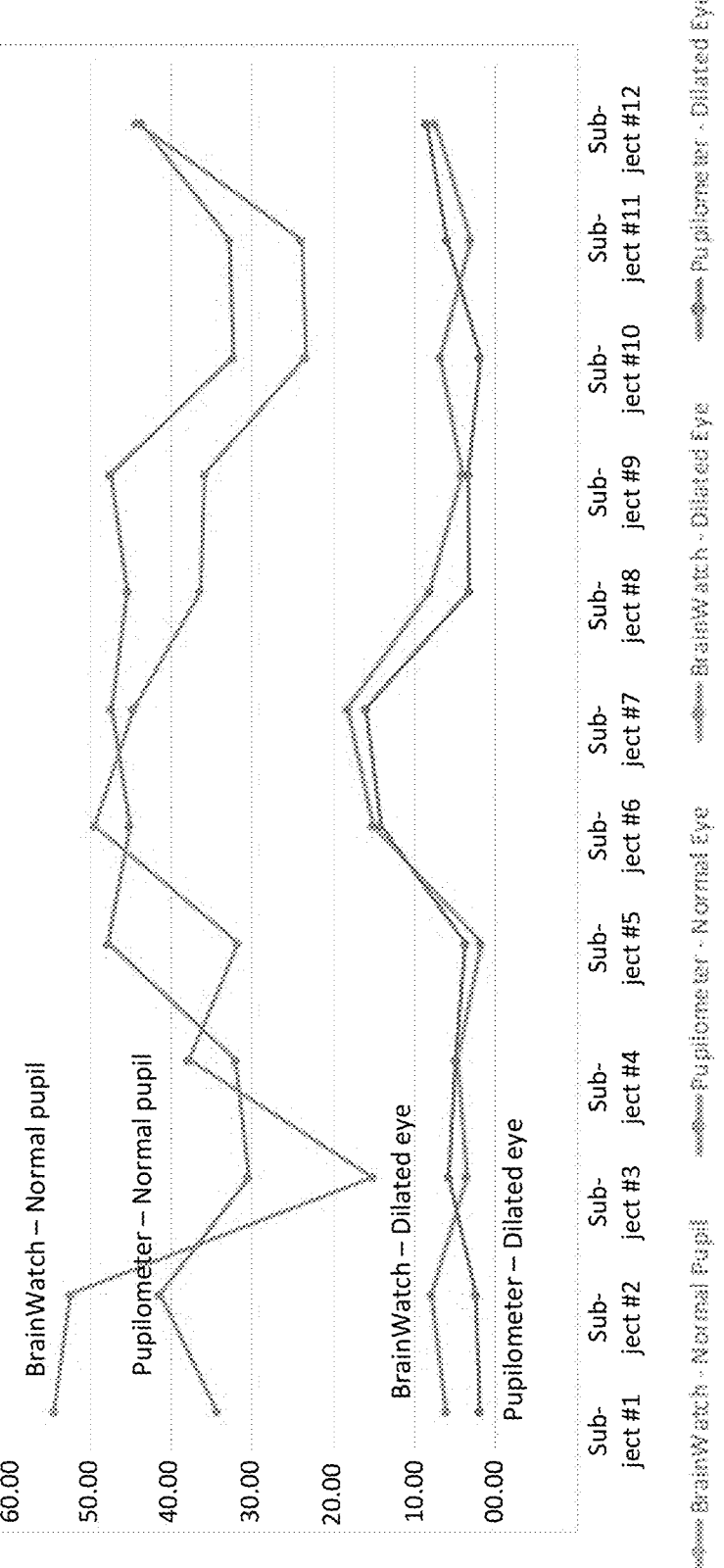
Figure 12:
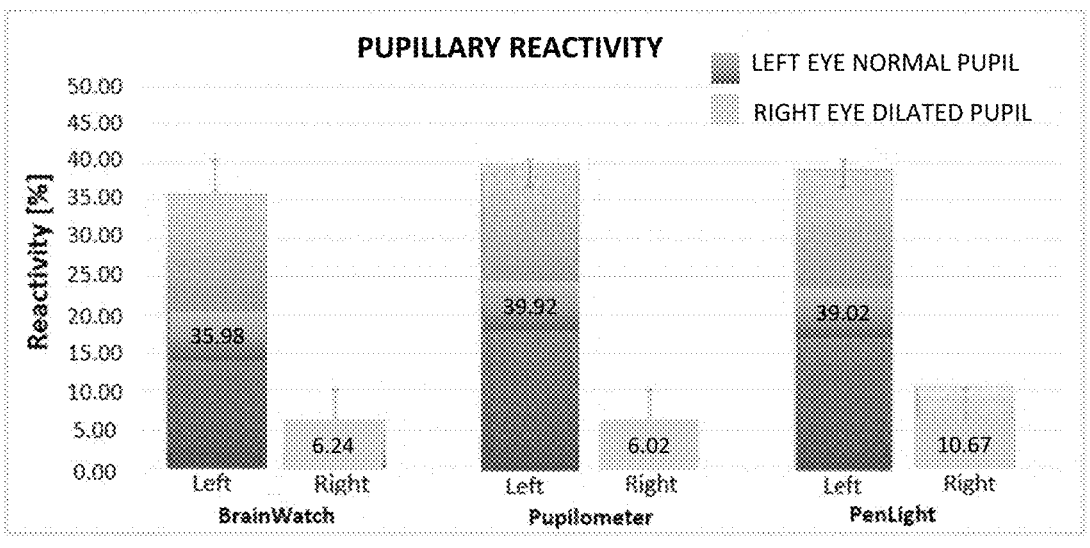
Figure 13:
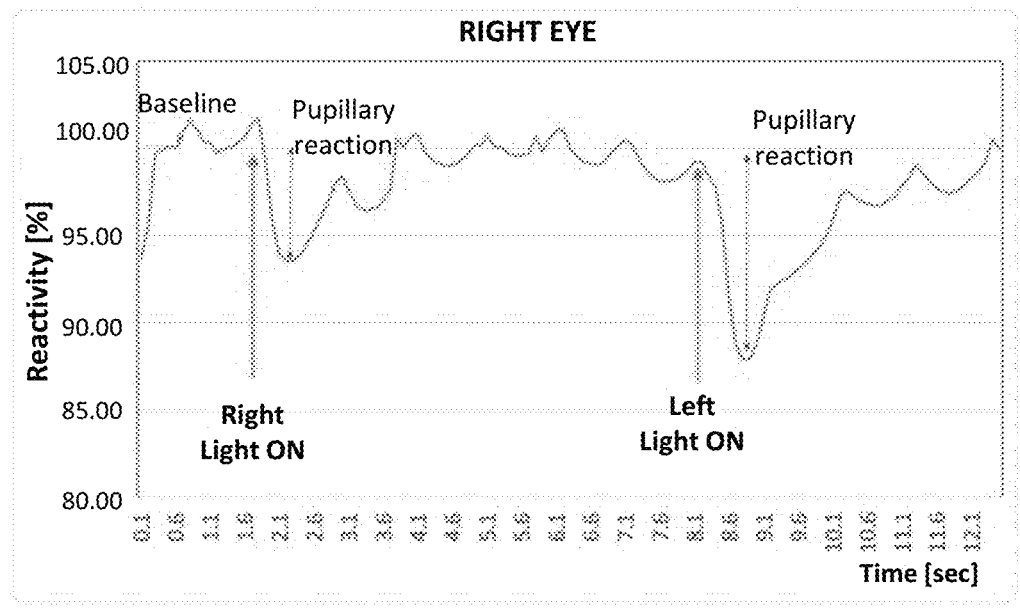

FIG. 10A shows a comparison of experimental results of the disclosed methods with the pupilometer method;

FIG. 10B shows a comparison of experimental results of the disclosed methods with the penlight method;

FIG. 10C shows a comparison of experimental results obtained by the pupilometer and the penlight techniques;

FIG. 11 shows a plot of the pupil reactivity of dilated and normal-sized eye obtained by the disclosed methods and by the pupilometer method;

FIG. 12 shows a summary of experimental results comparing the average pupillary reactivity; and FIG. 13 shows an experimental plot of the pupil reactivity as a function of time.

DETAILED DESCRIPTION

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

As used herein, terms "patient" and "subject" may refer to any individual for which determining a pupil size and/or pupillary reflex is of medical relevance. According to some embodiments, the patient may be a head trauma patient, a patient undergoing brain surgery, patients with ischemic or hemorrhagic stroke/event, patients in a coma, patients with encephalopathy following liver transplantation or surgeries; patients in emergency care such as in an ambulance; multiple trauma patients undergoing other surgeries such as fracture fixation, vascular repair, abdominal interventions; patients with brain infections; encephalopathy patients suffering from acute or chronic hepatic insufficiency/failure; encephalopathy following autoimmune processes involving brain vasculature or any other neurological condition.

According to some embodiments, the terms "patient" and "subject" may refer to an individual for which determining a pupil size and/or pupillary reflex is of medical relevance who may not suffer from a brain injury. For example, according to some embodiments, the patient may include an individual with a sleeping disorder. As used herein the terms "pupil size" and "pupil diameter" may be used interchangeably and refers to the size/diameter of the hole located in the center of the iris of the eye that allows light to strike the retina. As used herein the term "pupil size" may refer to a contour of the pupil. According to some embodiments, the term "pupil size" may refer to a contour of a segment associated with a pupil of the patient. As used herein the term "pupil size" may refer to an area within a contour of the pupil and/or a contour of a segment associated with a pupil of the patient. According to some embodiments, the determining of the pupil size may be performed in response to light being illuminated on the eye, also referred to herein as "pupillary light reflex". When bright light is illuminated on the eye, light sensitive cells in the retina, including rod and cone photoreceptors and melanopsin ganglion cells, will send signals to the oculomotor nerve, specifically the parasympathetic part coming from the Edinger-Westphal nucleus, which terminates on the circular iris sphincter muscle. When this muscle contracts, it reduces the size of the pupil. This is the pupillary light reflex, which is an important test of brainstem function. The normal pupil size in adults varies from 2 to 4 mm in diameter in bright light to 4 to 8 mm in the dark and is also known to vary between different individuals as well as with age.

As used herein the term "brain and/or nerve functions" may be used to describe types of indications and/or markers of a functionality of a patient. The term "brain and/or nerve functions" may refer to indicators associated with conditions such as brain damage secondary to stroke, hemorrhages, infections, tumors and/or head injury. The term "brain and/or nerve functions" may refer to indicators associated with conditions in which the patient may be partially responsive or unresponsive (such as, for example, under anesthesia) comatose, and/or asleep (such as, for example, while sleeping, e.g., in a sleeping lab).

As used herein the term "brain and/or nerve functions" may be used to describe one or more disorders of the brain and/or of nerves, such as, for example, Nerve CN II (or optic nerve), Nerve CN III (Oculomotor nerve) and other nerves in the pupillary light reflex pathway. A brain disorder may include a nystagmus, such as congenital, idiopathic, secondary to a pre-existing neurological disorder, drug induced or any combination thereof. An abnormal brain function may include deteriorations in the brain function, such as a result of brain herniation.

As used herein the term "frames" and "one or more frames" may refer to images, such as, for example, individual images within a video or a plurality of consecutive frames. The frames may include data associated with light transmittance, collected from and/or representing a pupil of a patient by capturing light transmitted through the pupil of the patient and through the closed eyelid of the patient. The term "one or more frames" may refer to multiple sequential still images, such as burst frames, or in other words, a series of succession images.

As used herein the terms "video" and "a plurality of frames" may be used interchangeably and refers to a plurality of frames captured within a time frame such that the motion and/or location of the pupil of the patient may be tracked therefrom. According to some embodiments, the video may include a plurality of frames. According to some embodiments, the plurality of frames may include two or more frames captured at intervals of 5 minutes, 4 minutes, 3 minutes, 2 minutes, 1 minutes, 45 seconds, 30 seconds, 15 seconds, 10 seconds, 6 seconds, 4 seconds, 2 seconds, 1 second, 600 milliseconds, 400 milliseconds, 200 milliseconds, 150 milliseconds, 100 milliseconds, 50 milliseconds, 35 milliseconds, 30 milliseconds, 25 milliseconds, 16 milliseconds, or any range therebetween. Each possibility is a separate embodiment.

According to some embodiments, the plurality of frames may be captured at a rate of 5-40 frames per second (fps). According to some embodiments, the plurality of frames may be captured at a rate of 10-30 fps. According to some embodiments, the plurality of frames may be captured at a rate of 10-35 fps. According to some embodiments, the plurality of frames may be captured at a rate of 5-15 fps. According to some embodiments, the plurality of frames may be captured at a rate of 5 fps, 7 fps, 10 fps, 11 fps, 13 fps, 15 fps, 17 fps, 20 fps, 23 fps, 25 fps, or 30 fps, or any range therebetween. Each possibility is a separate embodiment. According to some embodiments, the plurality of consecutive frames may be consecutive or semi-consecutive. According to some embodiments, the plurality of consecutive frames may be ordered chronologically. According to some embodiments, the plurality of consecutive frames may include a time stamp or time label associated with a time of capturing of each of the frames within the plurality of consecutive frames. According to some embodiments, the time stamp or time label of the plurality of consecutive frames may be relative to each other.

As used herein the terms "gray level" and "gray level value" may refer to a value associated with the brightness of a pixel within a frame, or the brightness of the light depicted by the pixel within the frame. The gray level may range between 0% and 100%, wherein the minimum grey level depicting essentially no light (or minimal light) transmittance is 0%. The maximum grey level, depicting maximal light transmittance is 100%. The gray level may range between a pixel value of 0 (depicting essentially no light) and a pixel value 255 (depicting maximal light intensity values). According to some embodiments, the gray level percent (0%-100%) may be equivalent and/or interchangeable with the gray scale values (0 to 255). For example, within the gray scale, a pixel value of 128 is equivalent to 50%.

As used herein the terms "segments" may refer to a plurality of pixels within a frame which share a common gray level value and/or a common range of gray level values.

As used herein the term "contour" may refer to a boundary line partitioning between a segment and the rest of the pixels within the frame.

Reference is made to FIG. 1, which shows a flowchart of functional steps in a method for determining a status of brain and/or nerve functions of a patient, in accordance with some embodiments of the present invention.

According to some embodiments, the method 100 may be configured to determine the status of brain and/or nerve functions of the patient by identifying and/or locating the pupil of the patient. According to some embodiments, the method 100 may be configured to determine the status of brain and/or nerve functions of the patient by calculating the size and/or the pupillary reflex of the pupil of the patient.

According to some embodiments, at step 102, the method 100 may include obtaining a video capturing light transmitted through a closed eyelid of the patient. According to some embodiments, at step 104, the method 100 may include identifying the pupil of the patient by analyzing an intensity of the light transmitted through the eyelid as captured in the video. According to some embodiments, at step 106, the method 100 may include tracking the position of the identified pupil of the patient. According to some embodiments, at step 108, the method 100 may include determining a status of brain and/or nerve functions of the patient may be based, at least in part, on the tracked location of the identified pupil of the patient.

According to some embodiments, the method 100 may include implementing a device for examining a pupil of a patient and/or a system for examining a pupil of a patient having closed eyelids, such as described in greater detail elsewhere herein. According to some embodiments, the method 100 may include emitting light toward a vitreous cavity of the patient using one or more light sources.

According to some embodiments, the method 100 may include emitting light within the spectrum of near Infra-Red (IR) range, about 700 to about 1500 nm or higher wavelengths. Each possibility is a separate embodiment. According to some embodiments, the method 100 may include emitting light within the range of 400-750 nm, 650-1500 nm, 700-1400 nm, 750-1200 nm, 750-1000 nm, 800-1000 nm or any other suitable range. Each possibility is a separate embodiment. According to some embodiments, the method 100 may include emitting light at a wavelength and/or intensity, which does not affect the pupils' diameter, also referred to herein as "non-inductive light". According to some embodiments, the method 100 may include emitting light at a wavelength and/or intensity enabling its transmission through the patient's head to the vitreous cavity without heating or causing damage to surrounding tissue. According to some embodiments, the method 100 may include emitting light using LED. According to some embodiments, the method 100 may include emitting light using a laser. According to some embodiments, the method 100 may include emitting light using a lamp.

According to some embodiments, the method 100 may include recording the light emitted by the one or more light sources through the closed eyelid of the patient. According to some embodiments, the recording may include a video and/or a plurality of frames. According to some embodiments, the method 100 may include capturing a video of the light emitted by the one or more light sources through the closed eyelid of the patient, such that the light captured in the video may be the light emitted by the one or more light sources. According to some embodiments, the method 100 may include capturing the video in real time. According to some embodiments, the method may include capturing one or more frames of the light transmitted from the one or more light sources through the closed eyelid of the patient.

According to some embodiments, at step 102, the method 100 may include obtaining a video capturing light transmitted through a closed eyelid of the patient. According to some embodiments, the method 100 may include obtaining the video from a video capturing device, an image capturing device, and/or a detector as described in greater detail elsewhere herein.

According to some embodiments, the method 100 may include preprocessing the video and/or at least a portion of the plurality of frames of the video. According to some embodiments, the preprocessing may include any one or more of adjusting the brightness, contrast, hue, saturation, sharpness, and gamma of the video. Each possibility is a separate embodiment. According to some embodiments, the preprocessing may include frame rate conversion. According to some embodiments, the preprocessing may include removing one or more frames of the video.

According to some embodiments, the method 100 may include obtaining the video in a grayscale format. According to some embodiments, the method 100 may include transforming the video into a grayscale format.

According to some embodiments, the method 100 may include transforming the video into a binary image (or black and white image). According to some embodiments, the transforming may include setting a binary threshold for transforming the image/s to a binary (black and white) format. According to some embodiments, the method may include setting a binary threshold for transforming the image/s to a binary (black and white) format. According to some embodiments, the binary threshold may be a grayscale value. According to some embodiments, the method may include transforming pixel values within the image which are below the binary threshold to a single pixel value (e.g., 0). According to some embodiments, the method may include transforming pixel values within the image which are above the binary threshold to a single pixel value (e.g., 255). According to some embodiments, the method may include determining more than one threshold. According to some embodiments, the more than one threshold may include at least one minimal threshold and at least one maximal threshold. According to some embodiments, the method may include setting the more than one threshold (or in other words, applying the more than one threshold to one or more frames of the video). According to some embodiments, the method may include removing the pixels (or the gray level values from pixels) in which the gray level values are below the minimal threshold. According to some embodiments, the method may include removing the pixels (or the gray level values from pixels) in which the gray level values are above the maximal threshold. For example, for a minimal threshold of 170, the method may include removing the pixels (or the gray level values from pixels) in which the gray level values are 169 and lower. For example, for a maximal threshold of 250, the method may include removing the pixels (or the gray level values from pixels) in which the gray level values are 251 and higher.

According to some embodiments, the method may include automatically removing the pixels (or the gray level values from pixels) below and/or above the minimal threshold and/or the maximal threshold, respectively.

According to some embodiments, the method may include identifying a specific pattern associated with escaping light, such as light escaping from the side or the eye or light that is emitted from the light sources but no transmitted through the tissue of the patient. According to some embodiments, the method may include applying one or more frames of the video to an algorithm configured to identify and/or remove the specific pattern. According to some embodiments, the algorithm may be a machine learning algorithm. According to some embodiments, the machine learning algorithm may be trained using supervised learning methods. According to some embodiments, the method may include receiving user input for identifying the specific pattern.

According to some embodiments, the video may include a plurality of frames, wherein each frame includes a plurality of pixels, such that each of the pixels of the plurality of frames may have a gray level value associated with light intensity.

According to some embodiments, the method 100 may include setting/defining a threshold for one or more of the plurality of frames such that the pupil is defined according to the baseline size.

According to some embodiments, the plurality of frames may include a first at least one frame, and a second at least one frame. According to some embodiments, the threshold may be defined for the first at least one frame such that the pupil size is defined according to the baseline size. According to some embodiments, the threshold of the first at least one frame may be used for determining the size of the pupil in the second at least one frames (e.g., the second at least one frame may include frames of the pupil having different sizes, positions, states, and the like).

According to some embodiments, the method 100 may include normalizing the images of the frames within the video. According to some embodiments, the method 100 may include smoothing the images of the frames within the video. According to some embodiments, the method 100 may include making one or more adjustments within the frames of the video. As a non-limiting example of an adjustment, folds of the skin of the eyelid and/or blood vessels in the eyelid may be accounted for. According to some embodiments, the method may include making one or more adjustments within the frames of the video such that uneven portions of the skin of the eyelid are accounted for.

According to some embodiments, at step 104, the method 100 may include identifying the pupil of the patient by analyzing an intensity of the light transmitted through the eyelid as captured in the video. According to some embodiments, the identifying of the pupil of the patient and/or the analyzing of the intensity of the light transmitted through the eyelid as captured by the video may be done in real time. According to some embodiments, the analyzing of the intensity of the light transmitted through the eyelid may include acquiring and/or analyzing the gray level of the pixels of frames within the video. According to some embodiments, the analyzing of the of the intensity of the light transmitted through the eyelid, and/or analyzing the gray level of the pixels of frames within the video, may include applying segmentation techniques to one or more frames within the video.

According to some embodiments, the method may include obtaining one or more frames in the form of still images while capturing the video (or in addition to the capturing the video). According to some embodiments, the method may include obtaining one or more frames in the form of still images instead of capturing a video. According to some embodiments, the one or more frames may include multiple still images. According to some embodiments, the one or more frames may be sequential. According to some embodiments, the one or more frames may include burst frames, or in other words, a series of succession images.

According to some embodiments, the plurality of frames may be captured at a speed in which the frames are about 10 milliseconds, 16 milliseconds, 20 milliseconds, 25 milliseconds, 30 milliseconds, 35 milliseconds, 45 milliseconds, 55 milliseconds, 75 milliseconds, 100 milliseconds, 150 milliseconds, 200 milliseconds, 400 milliseconds, or 600 milliseconds apart, or any range therebetween. Each possibility is a separate embodiment.

Advantageously, using one or more frames may increase the quality of the frames, thereby increasing the accuracy of the measurements and/or calculations of the size, movements, and/or shape of the pupil. Advantageously, using one or more frames may decrease the time that is required to analyze and output the measurements and/or calculations of the size, movements, and/or shape of the pupil.

According to some embodiments, the method may include analyzing the one or more frames such as described in greater detail elsewhere herein. According to some embodiments, the method may include analyzing the one or more frames so as to calculate any one or more of the size of the pupil, the shape of the pupil, and/or movements of the pupil of the patient, such as described in greater detail elsewhere herein.

According to some embodiments, the method may include comparing between the calculated size, shape and/or movements of the pupil of the subject from the one or more frames with the calculated size, shape and/or movements of the pupil of the subject from the video (or frames of the video).

Advantageously, the method and system described herein may therefore rely on and use either video or still frames, or both, to analyze the pupils, using the best of each output.

Figure 2A:
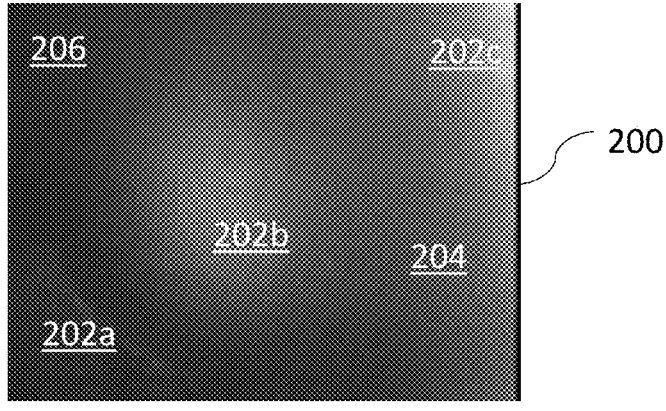

According to some embodiments, the method may include identifying the pupil of the patient within the video and/or one or more frames of the video. According to some embodiments, the method may include tracking the pupil of the patient within the video and/or one or more frames of the video. According to some embodiments, the method may include determining if the position of the pupil is an adequate position for obtaining one or more frames of still images. According to some embodiments, if the position of the pupil is an adequate position for obtaining one or more frames of still images, the method may include stopping the video and capturing one or more frames (or still images). According to some embodiments, the method may include continuing in capturing the video after obtaining the one or more frames. According to some embodiments, the method may include stopping the capturing of the video, capturing one or more frames (or still images) and the continuing capturing the video a plurality of times. According to some embodiments, the method may include stopping the capturing of the video in order to capture one or more frames once a specific pupil size is detected and/or identified. According to some embodiments, the method may include stopping the capturing of the video in order to capture one or more frames for a pupil that is identified as being in a constricted state. Reference is made to FIG. 2A, which shows a frame from an exemplary plurality of consecutive frames, in accordance with some embodiments of the present invention, and to FIG. 2B, which shows a frame from an exemplary plurality of consecutive frames with identified segmentations, in accordance with some embodiments of the present invention.

According to some embodiments, the method 100 may include identifying one or more segments within one or more frames. According to some embodiments, the one or more segments may include segments wherein the pixels associated with each segment have similar gray level values. According to some embodiments, the segments may include one or more local maxima segments, wherein the similar gray level values may include a plurality of pixels identified as having the highest gray level values within a portion of the frame. As used herein the term similar gray levels may refer to two or more gray level values (each being a gray level value of a pixel) which have the same value (between 0 and 255 and/or 0% to 100%). As used herein the term similar gray levels refers to two or more gray level values (each being a gray level value of a pixel) which have the same value (between 0 and 255 and/or 0% to 100%). As used herein the term similar gray levels may refer to two or more gray level values (each being a gray level value of a pixel) which are within a same range of values, or in other words, values which are within a specific deviation from a gray level value. According to some embodiments, the gray level values may be within a range of about 5%. According to some embodiments, the gray level values may be within a range of about 10%. According to some embodiments, the gray level values may be within a range of about 15%. According to some embodiments, the gray level values may be within a range of about 20%. According to some embodiments, the gray level values may be within a range of about 5%, 7%, 10%, 14%, 15%, 18%, 20%, 23%, or 25%, or any range therebetween. Each possibility is a separate embodiment.

According to some embodiments, the method may include determining a range, or the specific deviation, within which two pixels area considered to be similar. According to some embodiments, the range, or the specific deviation, within which two pixels area considered to be similar, or in other words, belonging to a same segment, may vary. According to some embodiments, the range, or distribution, within which two pixels area considered to be similar, may vary in correlation with the size of the pupil of the patient. According to some embodiments, the range (or specific deviation) may vary because different pupil sizes may have different ranges of distributions of gray levels. For example, larger pupils may have larger distributions of gray levels than smaller pupils, which may have smaller distributions. According to some embodiments, these distributions may differ from the surrounding (or background) of the segment (e.g., for example, the area around the pupil) which may have pixels with gray level values within ranges of 5%, 10%, 15%, 20%, or any range therebetween, in relation to one or more pixels within the segment of the pupil. For example, the pupil may be identified as a segment having a grey level of about 85% in the center and about 40% around the perimeter of the pupil, and the background around the pupil may have a gray level of about 35%. According to some embodiments, the gray levels of the background may be constant, and/or essentially the same, regardless of the size of the pupil of the patient.

According to some embodiments, the method may include determining the range, or the specific deviation, within which two pixels area considered to be similar, wherein the range and/or the specific deviation of different pupil sizes may be different. According to some embodiments, the method may include determining the range, or the specific deviation, separately for individual frames of the video.

According to some embodiments, different local maxima segments may include different values of gray levels of the pixels. For example, portion 202a of frame 200 may be identified as a local maxima segment in which the gray level values range between 60 to 70% while portions 202b and 202c may be identified as local maxima segments in which the gray level values are above 70%, while the surrounding pixels (such as within the portions 204 and 206) may have grey levels below 60%. According to some embodiments, the local maxima may include a local flat maxima, wherein the pixels may include a same gray level value. According to some embodiments, the similar gray level values may include gray level values above a predetermined maximum threshold. According to some embodiments, the predetermined maximum threshold may vary include predetermined rate of change of the gray level values throughout neighboring pixels. According to some embodiments, the predetermined maximum threshold may include a gray level value above 80%, 85%, or 90% intensity. Each possibility is a separate embodiment. According to some embodiments, the method 100 may include identifying one or more of the segments based on one or more distributions of the gray levels of pixels within the one or more segments. According to some embodiments, the one or more distributions may include a gaussian distribution.

Figure 2B:
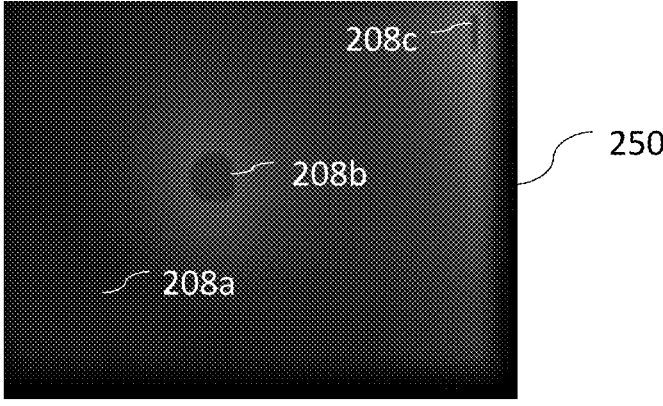

According to some embodiments, the method 100 may include contouring at least one of the segments, such as the marked segments 208a, 208b, and 208c depicted in frame 250 of FIG. 2B, which correspond to the identified segments 202a, 202b, and 202c of FIG. 2A, respectively. According to some embodiments, the contour may include one or more boundaries configured to define the perimeter of the one or more segments. According to some embodiments, the method 100 may include determining a shape of the at least one segment. According to some embodiments, the method 100 may include determining a shape of the at least one segment by determining a shape of the contour of the segment. According to some embodiments, the method 100 may include determining a gray level distribution within the at least one segment. According to some embodiments, the method 100 may include determining a gray level distribution within the contour of the segment. According to some embodiments, the gray level distribution may include a distribution of the gray level values. According to some embodiments, the method 100 may include determining a maximal gray level value within the at least one segment. According to some embodiments, the method 100 may include determining a maximal gray level value within a boundary of the contour of the at least one segment.

According to some embodiments, the method 100 may include identifying of the pupil of the patient based, at least in part, on the shape of the at least one segment. According to some embodiments, the method 100 may include identifying of the pupil of the patient based, at least in part, on the gray level distribution within the at least one segment. According to some embodiments, the method 100 may include identifying of the pupil of the patient based, at least in part, on the maximal gray level value within the at least one segment.

According to some embodiments, the method may include identifying two or more segments as the same pupil, wherein the two or more segments may be each within a different frame of the video. According to some embodiments, the method may include identifying two or more segments as the same pupil, wherein the two or more segments may be each within a different frame of the video and wherein the two or more segments may have different shapes, different areas, different sizes, different gray level values of the pixels within the segment, and/or different gray level distributions of the pixels within the segment. Each possibility is a separate embodiment.

Throughout the video, the individual frames within the video may depict different individual segments associated with a same pupil of the patient, wherein the pupil size may be different in two or more of the individual segments. Accordingly, the pupil of the patient may change in size which may change the intensities and/or distributions of the gray levels of the pixels within the segments associated with the pupil within the individual frames of the video. According to some embodiments, different positions of the pupil within the eye may affect the intensity, size, and/or distribution of the gray levels of the pixels within the segments associated with the pupil within the individual frames of the video.

According to some embodiments, the method may include determining the area of the segment associated with the pupil of the patient. According to some embodiments, the method may include identifying a change in any one or more of the area, shape, intensity and/or distribution of the gray levels of the pixels within the segments associated with the pupil within the individual frames of the video, wherein the change may be between different individual frames of the video. According to some embodiments, the method may include determining if a change, in any one or more of the area, shape, intensity and/or distribution of the gray levels of the pixels within the segments associated with the pupil within the individual frames of the video, is associated with a change in pupil size of the patient.

According to some embodiments, the method may include determining if a change, in any one or more of the area, shape, intensity and/or distribution of the gray levels of the pixels within the segments associated with the pupil within the individual frames of the video, is associated with a change in the location of the pupil of the patient. According to some embodiments, different locations of the pupil of the patient may be associated with different viewing directions of the pupil. According to some embodiments, the method may include identifying whether a change, in any one or more of the area, shape, intensity and/or distribution of the gray levels of the pixels, is caused by a change in the pupil size of the patient and/or caused by a change in the location (or viewing direction) of the pupil, by comparing the data associated with the change with data of the emitted light.

According to some embodiments, for a change, in any one or more of the area, shape, intensity and/or distribution of the gray levels of the pixels, that occurs around about the same time as the emission of light towards the vitreous cavity of the patient, the method may include identifying the change as being caused by a change in the pupil size of the patient. According to some embodiments, for a change, in any one or more of the area, shape, intensity and/or distribution of the gray levels of the pixels, that does not occur around about the same time as the emission of light towards the vitreous cavity of the patient, the method may include identifying the change as being caused by a change in the location of pupil, or viewing direction, of the patient.

According to some embodiments, the method may include choosing one or more frames within the video, for which the segment of the pupil will be identified. According to some embodiments, the method may include calculating any one or more of the area, shape, and/or size of the segment associated with the pupil for segments associated with a pupil that is in an ideal position for which the calculations may be of greater accuracy. According to some embodiments, the ideal position for which the calculations may be of greater accuracy may be a central position of the pupil. For example, according to some embodiments, the method may include identifying a pupil that is in a temporal and/or nasal position, and then waiting for the pupil to move back into a central position before calculating any one or more of the area, shape, and/or size of the segment associated with the pupil. According to some embodiments, the method 100 may include classifying the segment into types of segments based at least in part, on the shape of the at least one segment, the gray level distribution within the at least one segment, and the maximal gray level value within the at least one segment. According to some embodiments, classifying the segment into types of segments may include types such as, but not limited to, a pupil of the patient, light transmitted from the side of the eye of the patient, and light that was transmitted through other portions of the face or skin of the patient.

According to some embodiments, a segment associated with and/or classified as the pupil of the patient may include a symmetrical shape such as rounded and/or circular, and/or elliptical shape. According to some embodiments, the segment associated with and/or classified as the pupil of the patient may include an asymmetrical shape. According to some embodiments, a segment associated with a pupil may include only a portion of a whole pupil, which may be depicted as an arc (or sector) of the pupil. According to some embodiments, the calculation of the size and/or location of the pupil may be based, at least in part, on the arc (or sector) of the pupil.

According to some embodiments, a segment associated with and/or classifies as the pupil of the patient may include a gaussian distribution of gray level values therein. According to some embodiments, a segment associated with and/or classifies as the pupil of the patient may include a gaussian distribution of gray level values therein, such that the pixels associated with a center of the pupil includes a local maximal gray level value. According to some embodiments, the maximal gray level value within a segment associated with and/or classifies as the pupil of the patient may include values lower than a maximal gray level value of any one or more of a segment associated with light transmitted from the side of the eye of the patient and a segment associated with light that was transmitted through other portions of the face or skin of the patient.

According to some embodiments, the method 100 may include contouring at least two segments for at least two frames of the video, wherein each of the at least two segments may be associated with a different frame of the at least two frames of the video. According to some embodiments, the at least two frames may be consecutive, or semi-consecutive frames. According to some embodiments, semi-consecutive frames may include two or more frames that may have one or more, or a few, frames therebetween, in chronological viewing of the video.

According to some embodiments, the method 100 may include determining the shapes of the at least two segments associated with the at least two frames of the video, as described hereinabove. According to some embodiments, the method 100 may include determining the shapes of the at least two segments associated with the at least two frames of the video, by determining the shapes of the contours of the segments. According to some embodiments, the method 100 may include determining the gray level distributions within the at least two segments associated with the at least two frames of the video. According to some embodiments, the method 100 may include determining the gray level distributions within the contours of the segments associated with the at least two frames of the video. According to some embodiments, the method 100 may include determining maximal gray level values within the at least two segments associated with the at least two frames of the video. According to some embodiments, the method 100 may include determining the maximal gray level values within the boundaries of the contours of the at least two segments associated with the at least two frames of the video.

According to some embodiments, the method 100 may include comparing between the at least two identified segments associated with different frames within the video. According to some embodiments, a segment may be identified as being associated with a pupil of the patient if the movement or change in the coordinates of the segment between two or more frames of the video can be identified as continuous.

According to some embodiments, the method may include identifying one or more frames in which the segment associated with the pupil may disappear due to movement of the pupil inwards, outwards, upward or downwards within the eye socket. According to some embodiments, the method may include identifying one or more frames in which the segment associated with the pupil may disappear (or in other words, one or more frames which do not include a segment associated with a pupil of the patient) due to the pupil of the patient being in a position in which the light transmitted through the pupil does not reach the image capturing module.

According to some embodiments, the method may include identifying the pupil of the patient within the video throughout a plurality of frames therein, regardless of one or more disappearances of the segment associated with pupil of the patient. According to some embodiments, the method may include tracking the coordinates and/or the location of the segment associated with the pupil and/or pupil of the patient. According to some embodiments, the method may include tracking the coordinates and/or the location of the segment associated with the pupil and/or pupil of the patient while taking into account one or more frames that do not include a segment associated with the pupil.

According to some embodiments, the method may include applying one or more machine learning algorithms to the data associated with the segment of the pupil of the patient. According to some embodiments, the method may include acquiring data including the size of the pupil of the patient with an open eyelid. According to some embodiments, the method may include calculating the size of the pupil of the patient while the eyelid is closed, at least in part, by applying the one or more machine learning algorithms to one or more frames of the video. According to some embodiments, the machine learning algorithm may be configured to determine a size of a pupil of the patient from the one or more frames of the video based, at least in part, on data associated with the acquired data associated with the size of the pupil of the patient with an open eyelid.

According to some embodiments, comparing of the at least two identified segments may include comparing between any one or more of the shapes of the at least two segments, the shapes of the contours of the at least two segments, the gray level distributions within the at least two segments, the gray level distributions within the contours of the segments (or in other words, a rate of change in gray level within the segments), and the maximal gray level values within the at least two segments and/or contours of the at least two segments. According to some embodiments, the method 100 may include identifying the type of segment based at least in part, on the comparison between the at least two identified segments associated with different frames within the video. For example, according to some embodiments, the method 100 may be configured to associate a type of gray level distribution with a type of segment, such as a pupil of the patient. According to some embodiments, the method 100 may include identifying of the pupil of the patient based, at least in part, on the comparison between the at least two identified segments.

According to some embodiments, the method 100 may include comparing the coordinates of pixels within the segment and/or the coordinated of the shape and/or gray level distribution of pixels within the segments. According to some embodiments, for consecutive or semi-consecutive frame within the video, comparing and/or tracking the coordinates of pixels within the segment and/or the coordinated of the shape and/or gray level distribution of pixels within the segments may allow tracking of the location of the pupil of the patient.

According to some embodiments, at step 106, the method 100 may include tracking the location of the pupil of the patient. According to some embodiments, the tracking of the position of the pupil may be done in real time. According to some embodiments, tracking of the position of the pupil may include tracking the location and/or coordinates of the center of the pupil. According to some embodiments, tracking of the position of the pupil may include tracking the location and/or coordinates of the contour of the pupil. According to some embodiments, the method 100 may include tracking a change in coordinates of the pixels within a segment identified as being associated with the pupil of the patient. According to some embodiments, the tracking of the pupil may include tracking the coordinates of the local maxima of the segment associated with the pupil of the patient.

According to some embodiments, the method 100 may include tracking a location of the pupil of the patient. According to some embodiments, the method 100 may include tracking a movement (or a degree of movement) of the pupil of the patient. According to some embodiments, the method 100 may include tracking characteristics of the movement of the pupil, such as any one or more of the speed, the direction, the duration and/or the increments of movement of the pupil of the patient. According to some embodiments, the method 100 may include inputting the recorded movement of the pupil and/or the tracked characteristics of the movement of the pupil into an algorithm configured to classify the movement of the pupil and/or the characteristics of the movement of the pupil.

According to some embodiments, the algorithm may be configured to classify the status of the brain and/or nerve functions of the patient based, at least in part, on the movement of the pupil and/or the characteristics of the movement of the pupil of the patient.

According to some embodiments, the method 100 may include classifying the status of the brain and/or nerve functions of the patient based, at least in part, on the tracked location of the identified pupil of the patient. According to some embodiments, the method 100 may include classifying the status of the brain and/or nerve functions of the patient based, at least in part, on the movement of the pupil and/or the characteristics of the movement of the pupil of the patient. According to some embodiments, at step 108, the method 100 may include determining a status of brain and/or nerve functions of the patient may be based, at least in part, on the tracked location of the identified pupil of the patient. According to some embodiments, the method 100 may include determining a status of brain and/or nerve functions of the patient may be based, at least in part, on any one or more of a frequency of the movement of the identified pupil of the patient, a duration of an abnormal movement the identified pupil of the patient, According to some embodiments, the method 100 may include classifying the status of the brain and/or nerve functions of the patient as normal or abnormal, based, at least in part, on the tracked location of the pupil of the patient. According to some embodiments, the method 100 may include classifying the type of abnormality of the abnormal status of the brain and/or nerve functions of the patient, wherein the abnormality may include a nystagmus. According to some embodiments, the nystagmus may be congenital, idiopathic, secondary to a pre-existing neurological disorder, drug induced or any combination thereof.

According to some embodiments, the method 100 may include indexing a status of pupillary activity and/or the status of brain and/or nerve functions of the patient by an index. According to some embodiments, the index may include indicating normal, abnormal, or otherwise defined pupillary activity of the patient. As a non-limiting example, the index may include indicating excellent, good, weak, and very weak pupillary activity. As another non-limiting example, the index may include indicating good, weak, and very weak pupillary activity. According to some embodiments, the index may include an indices range defined for each of pupillarity activity statuses. As a non-limiting example, the index may include the indices range of 0-20 indicating a good pupillary activity, the indices range of 20-50 indicating a weak pupillary activity, and the indices range of 50-100 indicating a very weak pupillary activity, and, optionally, indices above 100 indicating an extremely weak pupillary activity. It may be understood that the number of the indices ranges and the values and/or ranges of each of the indices ranges may vary. It may be understood by one skilled in the art that the indices ranges are associated/related with the relation type defined/chosen for defining thereof.

According to some embodiments, the index (also referred to as BrainWatch Index (BWI)) may be defined, among others, according to relation (1):

$$BWI = \frac{\text{Pupil Size}}{\text{Reactivity}} \qquad (1)$$

wherein the pupil size is defined by the size (e.g., in mm) of the pupil before constriction, and wherein the reactivity units include a fraction or percentage thereof.

According to some embodiments, the BrainWatch Index may be defined, among others, according to relation (2):

$$BWI = \frac{\text{Pupil Size} \times \text{Time}}{\text{Reactivity}} \qquad (2)$$

wherein the time parameter refers to time to a contraction onset.

According to some embodiments, the BrainWatch Index may be defined, among others, according to relation (3):

$$BWI = \frac{(\text{Pupil Size})^2 \times \text{Time}}{\text{Reactivity}^2} \qquad (3)$$

wherein the time parameter refers to time of a contraction onset.

According to some embodiments, the BrainWatch Index may be defined, among others, according to relation (4):

$$BWI = \frac{(\text{Pupil Size})^2}{\text{Reactivity}} \qquad (4)$$

wherein the time parameter refers to time of a contraction onset.

According to some embodiments, the BrainWatch Index may be defined, among others, according to relation (5):

$$BWI = \frac{\text{Pupil Size}}{\text{Reactivity}^2} \qquad (5)$$

wherein the time parameter refers to time of contraction onset.

According to some embodiments, increase in the pupil size of the patient (e.g., dilated, blown pupil, and the like), may lead to increase in the BrainWatch Index value. According to some embodiments, decrease in the reactivity (e.g., until reaching a non-reacting pupil), may lead to increase in the BrainWatch Index value. According to some embodiments, the BrainWatch Index may include a threshold value.

According to some embodiments, the method may include mapping of the eyes of the patient. According to some embodiments, the mapping may include light intensity mapping. As a non-limiting example, the mapping may include mapping of an infrared light intensity emitted from the eyes of the patient. According to some embodiments, the machine learning module may include and implement an algorithm for light intensity mapping of the eye to improve/ enhance the pupil examination. According to some embodiments, the algorithm for light intensity mapping may include a relative weight factor. According to some embodiments, the relative weight factor may be related to a pupil located near and/or far away from the one or more light sources. According to some embodiments, the relative weight factor may be considered in the machine learning techniques/ algorithms for determining the size of the pupil of the patient.

According to some embodiments, the patient may be a comatose patient, a sedated patient, a patient undergoing surgery, or a patient that is not unconscious and is in need of monitoring. According to some embodiments, the patient may be an individual who is not fully sedated. According to some embodiments, the patient may be an individual who cannot or will not respond to directions. According to some embodiments, the patient may be an individual undergoing a surgery in which he/she is conscious, such as, for example, awake brain surgery.

Advantageously, the methods described herein may replace other monitoring techniques that are currently used in surgeries, in which the patient is required to maintain his eyes open and to be monitored while remaining awake. Advantageously, the methods described herein enable the patient to sleep during the surgery and still be monitored, thereby enabling the patient to close his eyes during the surgery. Accordingly, the methods described herein thereby enable the reduction of stress for the patient during the surgery.

According to some embodiments, the methods described herein may monitor the pain and/or anesthesia levels of the patient. Advantageously, according to some embodiments, the methods described herein may monitor the pain level of the patient with closed eyelids. According to some embodiments, the pain level may be assessed based on monitoring of the pupillary responses (e.g., constriction response and/or dilation response of the pupils to a pain stimulus) of the patient. According to some embodiments, the method 100 may include identifying whether the patient suffers from pain or a sleep disorder. According to some embodiments, the method 100 may include identifying a level of depth of sedation of the patient. According to some embodiments, the method 100 may include generating and/or outputting an alarm if an abnormal brain and/or nerve functions are detected. According to some embodiments, the method 100 may include generating and/or outputting an alarm if an abnormal pupil movement is detected.

Reference is made to FIG. 3, which shows a flowchart of functional steps in a method for determining a status of brain and/or nerve functions of a patient, in accordance with some embodiments of the present invention. According to some embodiments, the method 300 may include any one or more steps of the method 100 as described hereinabove, and similarly, the method 100 as described hereinabove may include any one or more steps of the method 300.

According to some embodiments, the method 300 may be configured determine a status of brain and/or nerve functions of a patient having closed eyelids. According to some embodiments, at step 302, the method 300 may include obtaining a video capturing light transmitted through a closed eyelid of the patient, the video including a plurality of frames. According to some embodiments, at step 304, the method 300 may include identifying, for pixels within the video, a minimal gray level value throughout the video. According to some embodiments, at step 306, the method 300 may include generating a minimal gray level frame based, at least in part, on the identified minimal gray level values of the pixels.

According to some embodiments, at step 308, the method may include subtracting the gray level values of pixels within the minimal gray level frame from gray level values of corresponding pixels within the rest of the frames of the video, thereby generating a processed video. According to some embodiments, at step 310, the method 300 may include locating the pupil of the patient within at least one frame of the processed video. According to some embodiments, at step 312, the method 300 may include calculating the size of the pupil of the patient. According to some embodiments, at step 314, the method 300 may include determining a status of brain and/or nerve functions of the patient based, at least in part, on the calculated size of the pupil of the patient.

According to some embodiments, the method 300 may include implementing a device for examining a pupil of a patient and/or a system for examining a pupil of a patient having closed eyelids, such as described in greater detail elsewhere herein. According to some embodiments, the method 300 may include emitting light toward a vitreous cavity of the patient using one or more light sources. According to some embodiments, the method 300 may include emitting light within the spectrum of near Infra-Red (IR) range, about 700 to about 1500 nm or higher wavelengths. Each possibility is a separate embodiment. According to some embodiments, the method 300 may include emitting light within the range of 400-750, 650-1500 nm, 700-1400 nm, 750-1200 nm, 750-1000 nm, 800-1000 nm or any other suitable range. Each possibility is a separate embodiment.

According to some embodiments, the method 300 may include emitting light at a wavelength and/or intensity, which does not affect the pupils' diameter, also referred to herein as "non-inductive light". According to some embodiments, the method 300 may include emitting light at a wavelength and/or intensity enabling its transmission through the patient's tissue to the vitreous cavity without heating or causing damage to surrounding tissue. According to some embodiments, the method 300 may include emitting light using LED. According to some embodiments, the method 300 may include emitting light using a laser. According to some embodiments, the method 300 may include emitting light using a lamp.

According to some embodiments, the method 300 may include recording the light emitted by the one or more light sources through the closed eyelid of the patient. According to some embodiments, the recording may include a video and/or a plurality of frames. According to some embodiments, the method 300 may include capturing a video of the light emitted by the one or more light sources through the closed eyelid of the patient, such that the light captured in the video is the light transmitted through the eyelid (and emitted by the one or more light sources). According to some embodiments, the method 300 may include capturing the video in real time.

According to some embodiments, at step 302, the method 100 may include obtaining a video capturing light transmitted through a closed eyelid of the patient, wherein the video includes a plurality of frames. According to some embodiments, the method 300 may include obtaining the video from a video capturing device, an image capturing device, and/or a detector as described in greater detail elsewhere herein. According to some embodiments, the method 300 may include preprocessing the video and/or at least a portion of the plurality of frames of the video. According to some embodiments, the preprocessing may include any one or more of adjusting the brightness, contrast, hue, saturation, sharpness, and gamma of the video. Each possibility is a separate embodiment.

According to some embodiments, the preprocessing may include frame rate conversion. According to some embodiments, the preprocessing may include removing one or more frames of the video. According to some embodiments, the method 300 may include obtaining the video in a grayscale format. According to some embodiments, the method 300 may include transforming the video into a grayscale format. According to some embodiments, the video may include a plurality of frames, wherein each frame may include a plurality of pixels, such that each of the pixels of the plurality of frames may have a gray level value associated with light intensity.

According to some embodiments, the method 300 may include normalizing the images of the frames within the video. According to some embodiments, the method 300 may include smoothing the images of the frames within the video. According to some embodiments, the method 300 may include making one or more adjustments within the frames of the video such that folds of the skin of the eyelid and/or blood vessels in the eyelid are accounted for. According to some embodiments, the method 300 may include making one or more adjustments within the frames of the video such that uneven portions of the skin of the eyelid, and/or blood vessels in the eyelid, are accounted for.

According to some embodiments, at step 304, the method 300 may include identifying, for pixels within the video, a minimal gray level value throughout the video. According to some embodiments, the method 300 may include scanning frames within the video. According to some embodiments, the method 300 may include comparing the gray level values of two or more corresponding pixels, wherein corresponding pixels may include pixels having a same coordinate(s) in different frames and/or images. According to some embodiments, the method 300 may include storing data associated with a minimal gray level value of the two or more corresponding pixels within the frames of the video, such that the lowest gray level value for each individual pixel (coordinate) may be stored and/or recorded during the scanning of the frames. According to some embodiments, the method 300 may include scanning at least a portion of the frames of the video.

According to some embodiments, the method 300 may include scanning each of the frames of the video. According to some embodiments, at step 306, the method 300 may include generating a minimal gray level frame based, at least in part, on the identified minimal gray level values of the pixels. According to some embodiments, the minimal gray level frame may include pixels having gray level values which correlate and/or are equal to the lowest gray level value of their corresponding pixel (coordinate) within the video. According to some embodiments, the minimal gray level frame may be updated (or in other words, the values of the gray levels of the pixels within the minimal gray level frame may be updated) during the scanning of the frames of the video. According to some embodiments, the minimal gray level frame may be updated in real time.

According to some embodiments, at step 308, the method may include subtracting the gray level values of pixels within the minimal gray level frame from gray level values of corresponding pixels within the rest of the frames of the video, thereby generating a processed video.

Advantageously, generating a minimal gray level frame and subtracting the minimal gray level frame from one or more frames of the video allows the generating of a processed video and/or frame, in which the gray level distribution has lower standard deviation when calculating the size of the pupil of the patient. According to some embodiments, different pupil sizes generally result in different ranges of gray levels within the frames. According to some embodiments, the larger the pupil of the patient, the higher the gray level values of the pixels within the frames.

Advantageously, the minimal gray level frame that is generated throughout the video is used to enhance the image in order to remove the unwanted light (noise) from the frames. Accordingly, implementing the minimal gray level frame may be advantageous when the pupil moves, such that different areas of the frames may have different gray level values at different times throughout the video.

According to some embodiments, if no pupil movement or low pupil movement was detected, the method may include implementing a factor method. According to some embodiments, the method may include implementing a factor method (such as a linear factor, or other factor type) that emphasizes the gray level values around the pupil location and reduces gray level values in the surroundings of the pupil. Accordingly, the system and method described herein may be configured to identify the pupil's position, analyze if its moving or not, and implement one type of algorithm for a moving pupil and another when it doesn't move. Advantageously, implementing a factor method enables detection of the pupil of within the one or more frames and/or within the video even when the pupil doesn't move (or in other words, when the pupil stays in the same location in the eye).

Figure 4A:
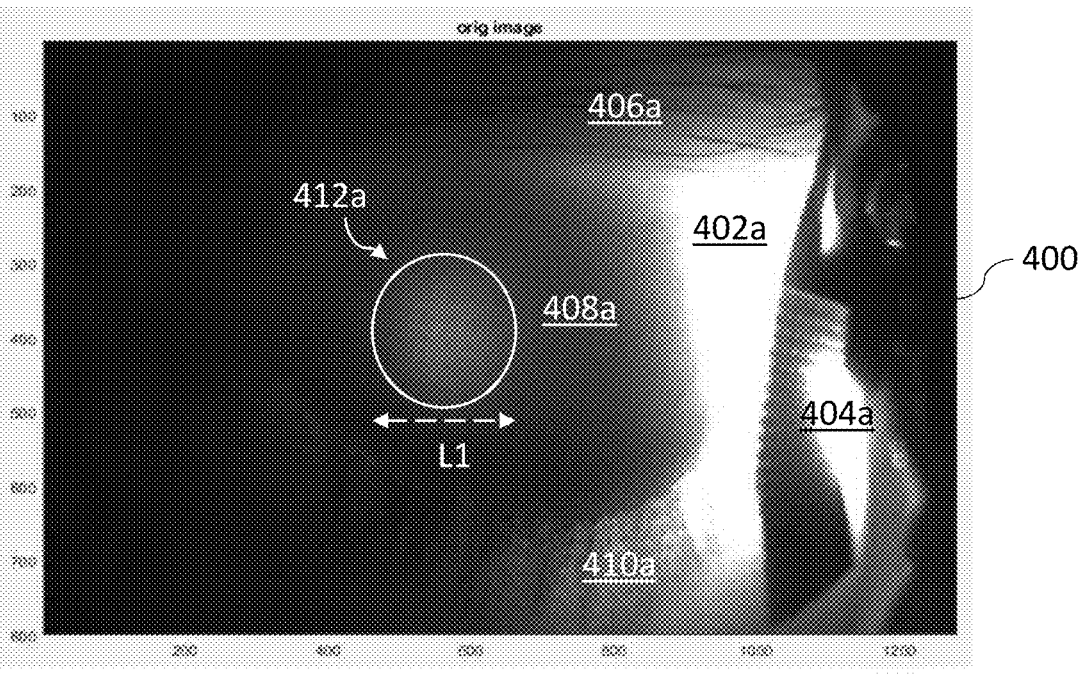
Figure 4B:
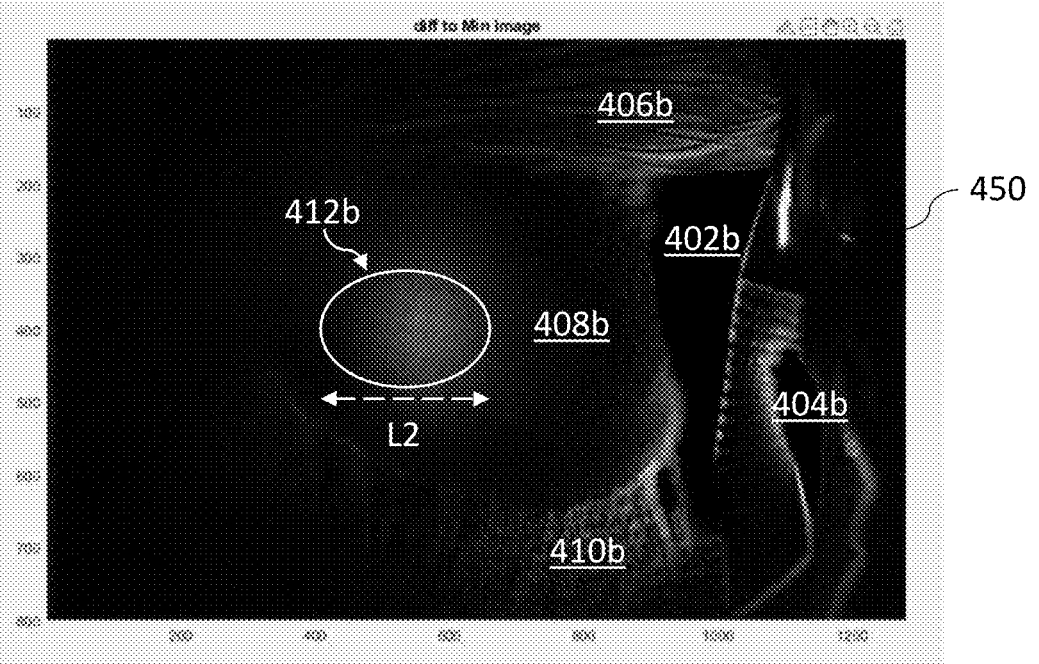

Reference is made to FIG. 4A, which shows a frame from an exemplary plurality of consecutive frames, in accordance with some embodiments of the present invention, and to FIG. 4B, which shows a frame from an exemplary plurality of consecutive frames after having a minimal gray level frame subtracted therefrom, in accordance with some embodiments of the present invention.

According to some embodiments, the method 300 may include generating one or more processed frames within the video by subtracting the minimal gray level frame from one or more frames within the video. According to some embodiments, the method 300 may include generating a processed video by subtracting the minimal gray level frame from the video (by subtracting the minimal gray frame from each of the frames of the video). According to some embodiments, subtracting the minimal gray level frame from a frame may include subtracting the values of the gray levels of the pixel within the minimal gray level frame from the values of the gray levels of the corresponding pixels within the frame.

According to some embodiments, subtracting the minimal gray level frame from one or more frames of the video enables removal of areas within the frames which may have a consistent gray level. For example, areas 402a, 404a, 406a, and 410a of frame 400 may have an overall high gray level value in corresponding pixels of other frames within the video, due to light that is transmitted and does not pass through the eyelid of the patient. Removal (or subtraction) of the gray level values of the pixels within areas 402a, 404a, 406a, and 410a may result in a processed frame, such as frame 450, in which the areas corresponding with areas 402a, 404a, 406a, and 410a (such as areas 402b, 404b, 406b, and 410b of frame 450) may include pixels having low gray level values.

According to some embodiments, once the gray level values of the pixels of such areas in the minimal gray level frame are subtracted from their corresponding areas in the frames of the video, the corresponding areas within the processed frames may include gray level values of essentially 0% (or essentially a gray level value of 0 within the range of 0 to 255). According to some embodiments, the processed frame may also include one or more areas, such as area 408a of frame 400, in which the gray level values may vary due to movement of the eyelid and/or the pupil of the patient. According to some embodiments, the removal (or subtraction) of the gray level values of the pixels of the minimal gray level frame from such areas may result in corresponding areas in the processed frame, such as area 408b of frame 450, in which the gray level values of the pixel area essentially 0%.

According to some embodiments, subtracting the minimal gray level frame from one or more frames of the video enables removal of gray level values of pixels depicted transmitted light in the immediate surrounding of the pupil of the patient, such as, for example, in the pixels in the corresponding areas 408a and 408b of frames 400 and 450, respectively. According to some embodiments, removal of gray level values of pixels depicted transmitted light in the immediate surrounding of the pupil enables removing light noise surrounding the pupil, such that in the processed frame and/or video the size of the pupil of the patient may have a smaller standard deviation in the measurement thereof.

For example, in frame 400, the area associated with the pupil of the patient is area 412a, and in the corresponding area 412b of the processed image 450, the diameter L1 of the area 412a before subtraction of the minimal gray level frame is substantially larger than the diameter L2 of the areas 412b after subtraction of the minimal gray level frame, wherein the removed gray level values from some of the pixels may be transmitted light from any one or more of movement of the pupil, light diffusion surrounding the pupil of the patient, and the like. Thus, according to some embodiments, removal of the minimal gray level frame from one or more frames of the video enables more precise calculation of the size of the pupil of the patient.

According to some embodiments, the method 300 may include identifying the pupil of the patient within the processed video and/or frame. According to some embodiments, at step 310, the method 300 may include locating the pupil of the patient within at least one frame of the processed video. According to some embodiments, locating of the pupil of the patient may include locating the center of the pupil of the patient. According to some embodiments, the method 300 may include tracking the location of the pupil of the patient throughout at least a portion of the video. According to some embodiments, and as described in greater detail elsewhere herein, the method 300 may include identifying the pupil of the patient by analyzing an intensity of the light transmitted through the eyelid as captured in the video. According to some embodiments, the identifying of the pupil of the patient and/or the analyzing of the intensity of the light transmitted through the eyelid as captured by the video may be done in real time.

According to some embodiments, the analyzing of the intensity of the light transmitted through the eyelid may include analyzing the gray level of the pixels of frames within the video. According to some embodiments, the analyzing of the of the intensity of the light transmitted through the eyelid, and/or analyzing the gray level of the pixels of frames within the video, may include applying segmentation techniques to one or more frames within the video. According to some embodiments, the method 300 may include identifying the pupil of the patient by contouring segments of the pupil, such as described in method 200. According to some embodiments, the method 300 may include identifying and/or tracking the location of the pupil of the patient, such as described in method 200 hereinabove.

According to some embodiments, the method 300 may include identifying at least one segment within at least one frame of the video as a segment associated with the pupil of the patient, such as described in greater detail elsewhere herein.

According to some embodiments, at step 312, the method 300 may include calculating the size of the pupil of the patient. According to some embodiments, the method may include calculating the size of the pupil before and/or after the light emission (or in other words, at a dilated state and/or a constricted state). According to some embodiments, the method may include calculating the size of the pupil before and/or after the light emission of a light in the visible range of wavelengths. According to some embodiments, the method 300 may include calculating the size of the pupil of the patient by determining a size of the contour and/or perimeter of the segment associated with the pupil of the patient. According to some embodiments, the method 300 may include calculating an area of the segment associated with the pupil of the patient. According to some embodiments, the method may include calculating an area of the segment associated with the pupil of the patient using a weighted index, wherein the weighted index may be in correlation with the distribution of gray level values (or in other words, the weighted index may be correlated with the light distribution of the light transmitted through the pupil of the patient).

According to some embodiments, the method may include a pupil light reflex (PLR) test. According to some embodiments, the PLR test may be implemented while the eyelid of the patient is closed. According to some embodiments, the PLR test may include checking a contraction and/or dilation of the pupil of the patient by turning the light off and/or on and monitoring the response of the pupil to the change in the light.

It is to be understood that referring to the size of the pupil may also refer to the gray level values within the segment associated with the pupil. Therefore, it is to be understood that calculating the size of the pupil may include analyzing the gray level values within the segment associated with the pupil. According to some embodiments, the method may include acquiring the gray level values within the segment associated with the pupil. According to some embodiments, the method may include calculating the size of the pupil based on the gray level values within the segment associated with the pupil of the patient. According to some embodiments, the method 300 may include monitoring changes in the pupil size, shape, and/or pupillary reflexes of the patient throughout at least a portion of the video and/or in real time. According to some embodiments, the monitoring of the changes in the pupil size, shape, and/or pupillary reflexes of the patient may include comparing the differences in the calculated pupil size and/or area of the segment associated with the pupil of the patient, within two or more frames within the video. According to some embodiments, the two or more frames may be consecutive and/or semi-consecutive frames.

According to some embodiments, the two or more frames may be nonsequential. According to some embodiments, the method 300 may include monitoring changes in the pupil size of the patient. According to some embodiments, the method 300 may include monitoring changes in the shape of the pupil of the patient. According to some embodiments, the method 300 may include calculating the pupillary contraction and dilation of the patient. According to some embodiments, the calculating the pupillary contraction and dilation of the patient may include calculating the difference between a minimal pupil size and a maximal pupil size within at least a portion of the video. According to some embodiments, the calculating the pupillary contraction and dilation of the patient may include calculating the difference between a minimal area of a segment associated with the pupil and a maximal area of a segment associated with the pupil within at least a portion of the video.

According to some embodiments, the video may include a plurality of maximal and/or minimal sizes of the pupil. According to some embodiments, the video may include a plurality of maximal and/or minimal areas of a segment associated with the pupil. According to some embodiments, the method 300 may include calculating the speed of contraction and/or dilation of the pupil of the patient. According to some embodiments, the method 300 may include calculating the change in the size of the pupil as a function of time. According to some embodiments, the calculating of the speed (or rate) of contraction and/or dilation may include measuring the time between the frame associated with the maximal pupil size and the frame associated with the minimal pupil size. According to some embodiments, the calculating of any one or more of the size of the pupil, the shape of the pupil, the speed of contraction and/or dilation of the pupil, and/or pupillary reflexes, may be evaluated and/or calculated in real time. Each possibility is a separate embodiment.

According to some embodiments, the method may include calculating any one or more of the size of the pupil, the shape of the pupil, the speed of contraction and/or dilation of the pupil, and/or pupillary reflexes using one or more identifiers and/or markers configured to calibrate the measurements and/or calculations. According to some embodiments, the one or more identifiers and/or markers may be positioned a certain distance from the eye of the patient. According to some embodiments, the method may include implementing one or more calibration methods configured to relate the frames within the video to a real-life scale, using the one or more identifiers and/or markers. According to some embodiments, the one or more calibration methods may include identifying the size of the one or more identifiers and/or markers. According to some embodiments, the calibration methods may include identifying the distance between the eye of the patient and the one or more identifiers and/or markers.

According to some embodiments, the video and/or one or more frames within the video may capture the one or more identifiers and/or markers. According to some embodiments, the one or more identifiers may include anatomical identifiers, such as, for example, the eyelashes of the patient. According to some embodiments, the one or more identifiers and/or markers may include a sticker or sensor positioned configured to be placed near the eye of the patient while capturing of the video. According to some embodiments, the method may include calculating any one or more of the size of the pupil and the shape of the pupil using the metric system, such as, for example, by calculating the size in millimeters and/or millimeters squared. According to some embodiments, the method 300 may include determining a baseline pupil size of the pupil of the patient prior to closing of the eyelid of the patient. According to some embodiments, the baseline pupil size may include a patient specific baseline, such as, for example, pupil size at time of hospitalization, pupil size prior to surgery, and/or pupil size before closing of the eyelid of the patient. According to some embodiments, the method 300 may include determining a baseline pupil size of the pupil of the patient by obtaining one or more images of the pupil of the patient.

According to some embodiments, the method 300 may include determining the baseline pupil size of the pupil of the patient by capturing one or more images of the pupil of the patient using non-inductive light (i.e., a light source emitting light having a wavelength and/or intensity, which does not induce a pupillary reflex). According to some embodiments, the baseline pupil size may include a large baseline size, indicative of a baseline size of a pupil in a dilated state thereof. According to some embodiments, the baseline pupil size may include a small baseline size, indicative of a baseline size of a pupil in a contracted state thereof. According to some embodiments, the calculation of the size of the pupil of the patient further may include taking into account the baseline pupil size.

According to some embodiments, at step 314, the method 300 may include determining a status of brain and/or nerve functions of the patient based, at least in part, on the calculated size of the pupil of the patient. According to some embodiments, the method 300 may include determining a status of brain and/or nerve functions of the patient based, at least in part, on any one or more of the size of the pupil, the shape of the pupil, the speed of contraction and/or dilation of the pupil, the tracked location of the pupil, the baseline pupil size, the speed (or velocity) of the pupils' movements, the direction of the pupils' movement, the pattern/sequence of the pupils' movement, and/or pupillary reflexes of the patient. Each possibility is a separate embodiment. According to some embodiments, the method 300 may include classifying the status of brain and/or nerve functions of the patient based, at least in part, on the calculated size of the pupil of the patient. According to some embodiments, the method 300 may include classifying the status of brain and/or nerve functions of the patient based, at least in part, on any one or more of the size of the pupil, the shape of the pupil, the speed of contraction and/or dilation of the pupil, the tracked location of the pupil, the baseline pupil size, the speed (or velocity) of the pupils' movements, the direction of the pupils' movement, the pattern/sequence of the pupils' movement, and/or pupillary reflexes of the patient. Each possibility is a separate embodiment.

According to some embodiments, the method 300 may include classifying the type of abnormality of the abnormal status of the brain and/or nerve functions of the patient, wherein the abnormality may include a nystagmus. According to some embodiments, the nystagmus is congenital, idiopathic, secondary to a pre-existing neurological disorder, drug induced or any combination thereof. According to some embodiments, the patient may be a comatose patient, a sedated patient and/or a patient undergoing surgery. According to some embodiments, the determining the status of the brain may include identifying whether the patient suffers from pain or a sleep disorder. According to some embodiments, the determining the status of the brain may include identifying a level of depth of sedation of the patient.

According to some embodiments, the method 300 may include generating an alarm if an abnormal brain and/or nerve functions is detected. According to some embodiments, the method 300 may include generating an alarm if any one or more of an abnormal pupil size, an abnormal change in the size of the pupil, an abnormal tracked location of the pupil, an abnormal movement of the pupil movement, and/or an abnormal pupil reflex is detected.

According to some embodiments, the method may include assessing if there is a difference between the two pupils (of the two eyes) of the patient. According to some embodiments, the difference between the two pupils may include any one or more of the sizes of the pupils, the shapes of the pupils, the speeds of contraction and/or dilation of the pupils, the tracked locations of the pupils, the baseline pupil sizes, the speeds (or velocities) of the pupils' movements, the directions of the pupils' movements, the patterns/sequences of the pupils' movements, and/or pupillary reflexes. According to some embodiments, the method 300 may include generating an alarm if there is a difference between pupils.

According to some embodiments, the method may include classifying the differences between the pupils as significant or non-significant. According to some embodiments, the method 300 may include generating an alarm if the difference between pupils is classified as significant. According to some embodiments, the method 300 may include classifying the status of brain and/or nerve functions of the patient based, at least in part, on the differences between the pupils. According to some embodiments, the method 300 may include classifying the type of abnormality of the abnormal status of the brain and/or nerve functions of the patient, based, at least in part, on the differences between the pupils. According to some embodiments, the alarm may be triggered if a change in the patient's pupil size and/or pupillary reflex is detected. According to some embodiments, the alarm may be triggered if an abnormal pupil size is detected. Additionally, or alternatively, the alarm may be triggered if an abnormal pupillary reflex is detected. According to some embodiments, the alarm may be triggered if the pupil size has changed by more than 2%, 5%, 10% or any other suitable percentage. Each possibility is a separate embodiment. According to some embodiments, the alarm may be triggered if the pupil size is determined to be more than 3.5, more than 4 mm, more than 4.5 mm in bright light. Each possibility is a separate embodiment According to some embodiments, the alarm may be triggered if a less than 1%, 21%, 5%, 10% or other suitable percentage change in the patient's pupil size is detected in response to a pupillary reflex test.

Figure 5:
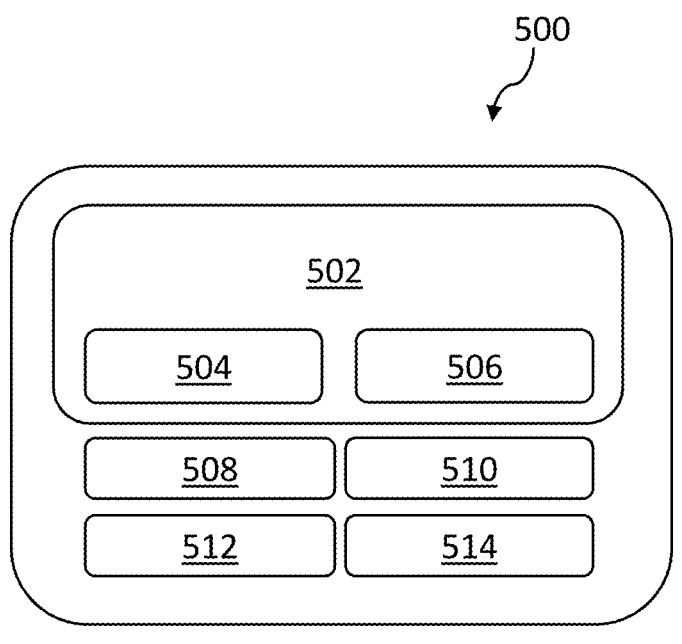

Reference is made to FIG. 5 shows a schematic illustration of a system for examining a pupil of a patient having closed eyelids, in accordance with some embodiments of the present invention.

According to some embodiments, the system 500 may be configured for examining a pupil of a patient. According to some embodiments, the system 500 may be configured for locating and/or tracking a pupil of a patient. According to some embodiments, the system 500 may be configured for calculating a size of the pupil of a patient. According to some embodiments, the system 500 may be configured for tracking one or more rates of change in the size of the pupil of a patient.

According to some embodiments, the system 500 may include at least one processing module 502, which may include at least one hardware processor. According to some embodiments, the processing module 502 may be in communication with at least one image capturing device 512 which may be configured to capture a video of a pupil of a patient through a closed eyelid of the patient, such as described in greater detail elsewhere herein. According to some embodiments, the system 500 may include a non-transitory computer-readable storage medium 504 having stored thereon program code and being in communication with the processing module 502. According to some embodiment, the program code may be executable by the at least one processing module 502. According to some embodiments, the processing module 502 and/or the storage medium 504 may be in operational communication with the image capturing device 512.

According to some embodiments, the system may include a device for examining a pupil of a patient. According to some embodiments, the device may include examining a pupil of a patient an image capturing device, such as the image capturing device 512 depicted in FIG. 5. According to some embodiments, the system 500 and/or the device for examining a pupil of a patient may include one or more light sources 514 for transmitting light through a vitreous cavity of the patient. According to some embodiments, the image capturing device 512 may be configured to obtain a video and/or a plurality of frames associated with the transmitted light through the closed eyelid of the patient. According to some embodiments, the image capturing device 512 may be configured to capture one or more images for calculating a baseline pupil size of the patient.

According to some embodiments, the one or more light sources 514 may be configured to emit light within the spectrum of near Infra-Red (IR) range, such as, about 750 nm to about 1500 nm. Each possibility is a separate embodiment. According to some embodiments, the one or more light sources may be configured to emit light within the range of 400-750 nm, 650-1500 nm, 750-1400 nm, 750-1200 nm, 750-1000 nm, 800-1000 nm or any other suitable range. Each possibility is a separate embodiment. According to some embodiments, the one or more light sources may be configured to emit light at a wavelength and/or intensity, which does not affect the pupils' diameter, also referred to herein as "non-inductive light". According to some embodiments, the one or more light sources may be configured to emit light at a wavelength and/or intensity enabling its transmission through the patient's head to the vitreous cavity without heating or causing damage to surrounding tissue. According to some embodiments, the device may further include an optical long pass filter (e.g., 800 nm) configured to reduce background light.

According to some embodiments, the one or more light sources 514 may be an LED. According to some embodiments, the one or more light sources may be a laser. According to some embodiments, the one or more light source may be a lamp. According to some embodiments, the one or more light sources may be a single light source. According to some embodiments, the single light source may be capable of emitting light reaching the vitreous cavity of both the patient's eyes, either simultaneously or consecutively (for example due to movement of the light source relative to the patient's eyes). According to some embodiments, the system may include two light sources e.g., a first light source configured to emit light towards the right vitreous cavity from the right temple of the patient and a second light source configured to emit light towards the left vitreous cavity from the left temple of the patient.

According to some embodiments, the system may include more than two light sources 514 such as 3, 4, 5 or more light sources. Each possibility is a separate embodiment. According to some embodiments, the device for examining a pupil of a patient and/or the image capturing device 512 may be in communication with the storage medium 504 and/or the processing module 502.

According to some embodiments, the one or more light sources 514 may be an inductive light source, (i.e., a light source transmitting light having a wavelength and/or intensity, which induces a pupillary reflex as described in greater detail elsewhere herein). According to some embodiments, the device and/or the one or more light sources may further include an inductive light source configured to emit inductive light (light capable of inducing a pupillary reflex), i.e., in the range of 400-700 nm. The visible light is configured to be emitted towards the patient's eye(s), through the closed eyelid(s) and is configured to induce the pupillary reflex. According to some embodiments, the storage medium of the system 500 may have stored thereon a program code including one or more algorithms configured to execute one or more of the method 100 and method 300 as described hereinabove. According to some embodiments, the storage medium of the system 500 may have stored thereon a program code including one or more algorithms configured to execute one or more steps of the method 100 and method 300 as described hereinabove. According to some embodiments, the storage medium of the system 500 may include a Read only memory (ROM) and/or random-access memory (RAM). According to some embodiments, the storage medium of the system 500 may include an external or internal DVD or CD ROM drive, a hard drive, flash memory, a USB drive, or the like. According to some embodiments, the storage medium of the system 500 may include a tangible computer readable medium such as a compact disk, a digital disk, flash memory, a memory card, a USB drive, an optical disc storage medium, such as a Blu-ray™ disc, and/or other recording medium. Each possibility is a separate embodiment.

According to some embodiments, the at least one hardware processor and/or the non-transitory computer-readable storage may be configured to receive the video and/or frames obtained by the image capturing module and/or device for examining the pupil of the patient. According to some embodiments, the at least one hardware processor and/or the non-transitory computer-readable storage may be configured to receive the video and/or frames in real time. According to some embodiments, the algorithm may be configured to preprocess the video and/or frames as described in the methods 100/300 hereinabove. According to some embodiments, algorithm may be configured to process the video and/or frames as described in the methods 100/300 hereinabove. According to some embodiments, the algorithm may be configured to remove irrelevant frames within the video, such as frames where the pupil of the patient does not show.

According to some embodiments, the one or more algorithms may be configured to identify the pupil of the patient by analyzing an intensity of the light transmitted through the eyelid as captured in the video. According to some embodiments, the one or more algorithms may be configured to identify the pupil of the patient in one or more frames in which only a portion of the pupil is visible, for example, such as in a frame in which half or more of the pupil is not visible through the eyelid of the patient, for example, when the pupil of the patient is positioned as if the patient is gazing down to their feet. According to some embodiments, the algorithm may be configured to track the location of the identified pupil of the patient in at least a portion of the video. According to some embodiments, the algorithm may be configured to track the location of the pupil in real time. According to some embodiments, the algorithm may be further executable to calculate the size of the pupil and/or pupillary reflex of a patient.

According to some embodiments, the algorithm may be configured to identify, for pixels within the video, a minimal gray level value throughout the video. According to some embodiments, the algorithm may be configured generate a minimal gray level frame based, at least in part, on the identified minimal gray level values of the pixels. According to some embodiments, the algorithm may be configured subtract the gray level values of pixels within the minimal gray level frame from gray level values of corresponding pixels within the rest of the frames of the video, thereby generating a processed video. According to some embodiments, the algorithm may be configured locate the pupil of the patient within at least one frame of the processed video. According to some embodiments, the algorithm may be configured calculate the size of the pupil of the patient.

According to some embodiments, the one or more algorithms may be configured to receive the video of the pupil of the patient. According to some embodiments, the algorithm may be configured to determine a status of brain and/or nerve functions of the patient is based, at least in part, on the tracked location of the identified pupil of the patient. According to some embodiments, the algorithm may be further executable to calculate the radius and/or diameter of the pupil and/or track the location of the pupil of the patient within the received video. According to some embodiments, the algorithm may be configured determine a status of brain and/or nerve functions of the patient based, at least in part, on the calculated size of the pupil of the patient.

According to some embodiments, the one or more algorithms may include one or more machine learning models 506. According to some embodiments, the one or more algorithms and/or one or more machine learning models 506 may be configured to classify the status of brain and/or nerve functions of the patient. According to some embodiments, the one or more machine learning models 506 may include one or more classifiers configured to receive any one or more of the video of the pupil of the patient, one or more frames of the pupil of the patient, one or more images associated with a baseline pupil size of the patient, the calculated baseline pupil size of the patient, the calculated pupil size of the patient, the tracked location of the pupil, the rate of change (or speed) of the contraction and/or dilation of the pupil of the patient, parameters (such as speed, direction, duration and/or frequency) of movement of the pupil of the patient, and pupillary reflex of the patient. Each possibility is a separate embodiment.

According to some embodiments, the one or more machine learning models 506 may be configured to classify the status of the brain and/or nerve functions of the patient based, at least in part, on any one or more of the video of the pupil of the patient, one or more frames of the pupil of the patient, one or more images associated with a baseline pupil size of the patient, the calculated baseline pupil size of the patient, the calculated pupil size of the patient, the tracked location of the pupil, the rate of change (or speed) of the contraction and/or dilation of the pupil of the patient, parameters (such as speed, direction, duration and/or frequency) of movement of the pupil of the patient, and pupillary reflex of the patient. Each possibility is a separate embodiment.

According to some embodiments, the one or more machine learning models 506 may be configured to classify the status of the brain and/or nerve functions of the patient based, at least in part, on data inputted by a user, such as a doctor or operator, wherein the data includes any one or more of the age, gender, blood pressure, eating habits, risk factors associated with specific disorders, genetic data, medical history of the family of the patient and medical history of the patient. According to some embodiments, the one or more machine learning modules 506 may be configured to extract one or more features from the video and/or frames. According to some embodiments, the one or more machine learning modules 506 may include using feature extraction techniques for dimensionality reduction. According to some embodiments, the machine learning modules 506 may be configured to process the video and/or frames.

According to some embodiments, the one or more machine learning modules 506 are trained using a training set. According to some embodiments, the training set may include a plurality of videos and/or one or more frames of pupils of a plurality of patients. According to some embodiments, the training set may include labels including data associated with a brain and/or nerve function of the patients depicted within the video and/or one or more frames. According to some embodiments, the data associated with a brain and/or nerve function may include an indication if the patient(s) depicted in the video and/or one or more frames suffer from one or more brain and/or nerve function disorder.

According to some embodiments, the one or more machine learning modules 506 may be configured for data extraction and analysis of any one or more of the video of the pupil of the patient, one or more frames of the pupil of the patient, one or more images associated with a baseline pupil size of the patient, the calculated baseline pupil size of the patient, the calculated pupil size of the patient, the calculated reactivity of the pupils, the tracked location of the pupil, the rate of change (or speed) of the contraction and/or dilation of the pupil of the patient, parameters (such as speed, direction, duration and/or frequency) of movement of the pupil of the patient, and pupillary reflex of the patient. Each possibility is a separate embodiment. According to some embodiments, the one or more machine learning modules 506 may include deep learning techniques. According to some embodiments, the one or more machine learning modules 506 may include, among others, data extraction by using artificial neural networks and/or convolutional neural networks and/or recurrent neural networks. According to some embodiments, the one or more machine learning modules 506 may include feature extraction. According to some embodiments, the one or more machine learning modules 506 may include pattern recognition. According to some embodiments, the one or more machine learning modules 506 may include supervised learning algorithm analyzes. According to some embodiments, the one or more machine learning modules 506 may include classification algorithms. According to some embodiments, the one or more machine learning modules 506 may include minimizing the cost function, such as but not limited to, gradient descent algorithm.

According to some embodiments, the data associated with a brain and/or nerve function may include an indication if the patient(s) depicted in the video and/or one or more frames suffer from a specific brain and/or nerve function disorder. According to some embodiments, the specific brain and/or nerve function disorder may include a type of brain function disorder, such as, for example, a nystagmus or a type of nystagmus. According to some embodiments, the specific brain and/or nerve function disorder may include a type of nerve disorder wherein the nerve is a nerve of the pupillary light reflex pathway of the patient, such as, for example, the nerve CN II and/or nerve CN III. According to some embodiments, the labels may include any one or more of the age, gender, blood pressure, eating habits, risk factors associated with specific disorders, genetic data, medical history of the family of the patient(s) depicted in the video(s) and/or one or more frames and medical history of the patient(s) depicted in the video(s) and/or one or more frames.

The one or more machine learning modules 506 may be validated and/or trained using one or more validation datasets and/or test datasets. According to some embodiments, the one or more validation datasets and/or test datasets may include a plurality of videos and/or one or more frames of pupils of a plurality of patients. According to some embodiments, the one or more validation datasets and/or test datasets may include labels including data associated with a brain and/or nerve function of the patients depicted within the video and/or one or more frames. According to some embodiments, the one or more validation datasets and/or test datasets may include an indication if the patient(s) depicted in the video and/or one or more frames suffer from one or more brain and/or nerve function disorder.

According to some embodiments, the one or more validation datasets and/or test datasets may include an indication if the patient(s) depicted in the video and/or one or more frames suffer from a specific brain and/or nerve function disorder. According to some embodiments, the one or more validation datasets and/or test datasets may include a type of brain function disorder and/or a type of nerve disorder wherein the nerve is a nerve of the pupillary light reflex pathway of the patient. According to some embodiments, the one or more validation datasets and/or test datasets may include the age, gender, blood pressure, eating habits, risk factors associated with specific disorders, genetic data, medical history of the family of the patient(s) depicted in the video(s) and/or one or more frames and medical history of the patient(s) depicted in the video(s) and/or one or more frames.

According to some embodiments, the system 500 may include a user interface module 508. According to some embodiments, the user interface module may be configured to receive data from a user or operator, such as, for example, age, gender, blood pressure, eating habits, risk factors associated with specific disorders, genetic data, medical history of the family of the patient and medical history of the patient. According to some embodiments, the user interface module may be configured to communicate with the processing module 502 such that the user inputted data is fed to the one or more machine learning modules 506. According to some embodiments, the user interface module may include at least one of a display screen and a button. According to some embodiments, the user interface module may include a software configured for transferring inputted information from a user to the processing module 502.

According to some embodiments, the user interface module may include a computer program and/or a smartphone application. According to some embodiments, the user interface module 508 may be include and/or be configured to receive data from input devices such as a keyboard or other input device such as a mouse, a joystick, a touch screen, a remote control, a display interface, a pointing device, a video input device and/or an audio input device. According to some embodiments, the user interface module may be configured to receive data from the processing module 502 and/or display data received from the processing module 502. According to some embodiments, the user interface module may be configured to display a result of a detection of an abnormality and/or a disorder. According to some embodiments, the user interface module may be configured to display one or more outputs of the one or more machine learning modules 506.

Figure 7:
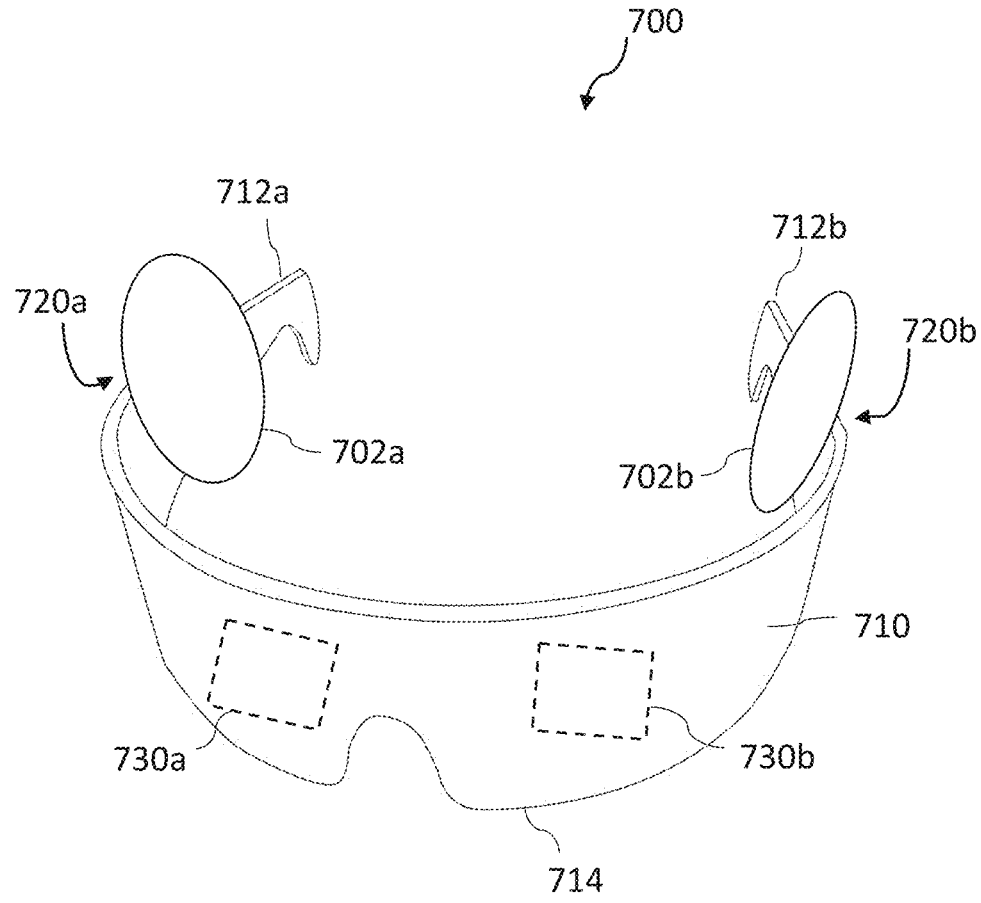

According to some embodiments, the device 510 may include a device for examining a pupil of a patient having closed eyelids, such as device 700 of FIG. 7 disclosed herein, such as an image capturing device.

Figure 6:
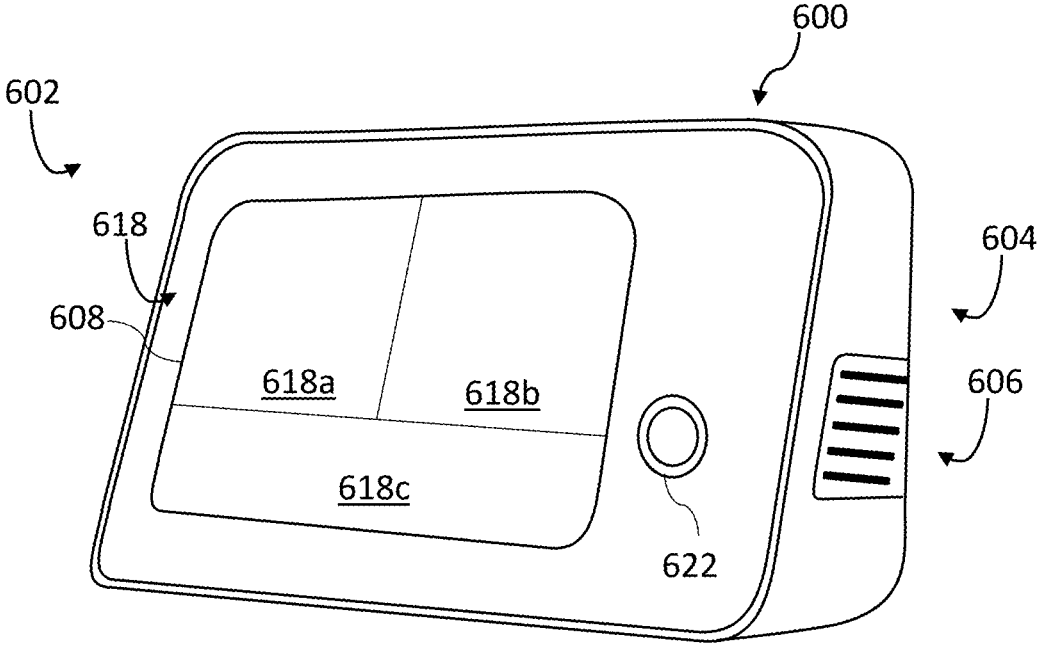

Reference is made to FIG. 6, which shows a schematic illustration of a system 600 for examining a pupil of a patient having closed eyelids, according to some embodiments.

According to some embodiments, the system 600 may be identical, similar or different from the disclosed herein system 500.

According to some embodiments, the system 600 may be configured for examining a pupil of a patient. According to some embodiments, the system 600 may be configured for locating and/or tracking a pupil of a patient. According to some embodiments, the system 600 may be configured for calculating a size of the pupils of a patient. According to some embodiments, the system 600 may be configured for determining the reactivity of the pupils of a patient. According to some embodiments, the system 600 may be configured for tracking one or more rates of change in the size of the pupil of a patient. According to some embodiments, the system 600 may be configured for determining movement of the pupil of a patient. According to some embodiments, the system 600 may be configured for determining the change in movement of the pupil of a patient.

According to some embodiments, the following components/features depicted in FIG. 6 602, 604, 606, and 608 correspond to and may have the same structure, configuration and/or characteristics as the previously described herein components 502, 504, 506, and 508 in FIG. 5.

According to some embodiments, the system 600 includes a user interface module 608. According to some embodiments, the user interface module 608 includes a display screen 618. According to some embodiments, the display screen 618 may include a first screen/region 618a and a second screen/region 618b configured for displaying the right and the left pupil of a patient, respectively.

According to some embodiments, the first and the second screen/regions 618a and 618b are configured to display a frame and/or consecutive frames after having a minimal gray level frame subtracted therefrom, such as depicted in FIG. 4A and/or FIG. 4B.

According to some embodiments, the first and the second screen/regions 618a and 618b are configured to display a processed image/video of the eyes of the patients, showing the pupil size and/or movement. According to some embodiments, image analysis algorithms and/or machine learning techniques may be applied for visualizing the eye/pupil movement According to some embodiments, the first and the second screen/regions 618a and 618b may display the pupil movement of the patient in real time. According to some embodiments, the visualizing includes natural eyes movement of the patient, thereby comforting visitors, including family members, relatives, friends, and the like. According to some embodiments, the system, 600 may be in a communication with a mobile application, comforting the visitors distant from the patient (e.g., outside a medical facility).

According to some embodiments, the display screen 618 includes a third screen/region 618c. According to some embodiments, the third screen/region 618c may be a touch sensitive screen, allowing adjusting of various parameters, such as brightness, contrast, and the like. According to some embodiments, the third screen/region 618c may be configured to receive data from a user or operator, such as, for example, age, gender, blood pressure, eating habits, risk factors associated with specific disorders, genetic data, medical history of the family of the patient and medical history of the patient. According to some embodiments, the user interface module 608 may be configured to communicate with a processing module 602 such that the user inputted data is fed to one or more machine learning modules 606. According to some embodiments, the user interface module 608 may include a software configured for transferring inputted information from a user to the processing module 602.

According to some embodiments, the user interface module 608 may include at least one button 622.

According to some embodiments, the user interface module 608 may include a computer program and/or a smartphone application. According to some embodiments, the user interface module 608 may be include and/or be configured to receive data from input devices such as a keyboard or other input device such as a mouse, a joystick, a touch screen, a remote control, a display interface, a pointing device, a video input device and/or an audio input device. According to some embodiments, the user interface module may be configured to receive data from the processing module 602 and/or display data received from the processing module 602. According to some embodiments, the user interface module may be configured to display a result of a detection of an abnormality and/or a disorder. According to some embodiments, the user interface module 608 may be configured to display one or more outputs of the one or more machine learning modules 606.

According to some embodiments, the system 600 may include or by in a communication with a device for examining a pupil of a patient having closed eyelids, such as device 700 of FIG. 7 disclosed herein, such as an image capturing device. Reference is made to FIG. 7 shows a schematic illustration of a device for examining a pupil of a patient having closed eyelids, in accordance with some embodiments of the present invention.

According to some embodiments, the device 700 may be configured for examining a pupil of a patient having closed eyelids. According to some embodiments, the device 510/700 may be configured for determining a pupil size, pupil movement, and/or pupillary reflex of a patient having closed eyelids. According to some embodiments, the device 510/700 may include one or more light sources configured to emit light toward a vitreous cavity of the patient through a temple of the patient. According to some embodiments, the device 510/700 may include a hood 702a/702b configured to minimize photon escape from the patient's temple. According to some embodiments, the hood 702a/702b may include an opening configured for passage of the emitted light. According to some embodiments, the device 510/700 may include one or more light detectors configured to detect an intensity of light exiting the patient's pupils in response to the emitted light.

According to some embodiments, the device 510/700 may include a platform unit used for wearing by the patient, such as the eyeglasses 710. According to some embodiments, the device 510/700 and/or the eyeglasses 710 may include frame temples 712a and 712b and a frame front 714. According to some embodiments, the device 510/700 may include one or more light sources. According to some embodiments, each of frame temples 712a and 712b may include a light source, such as the light sources 720a/514 and 720b/514 configured to transmit light through the side of a patient's head to the vitreous cavity. According to some embodiments, the frame front 714 may be made from a material impermeable to light and includes light detectors 730a and 730b positioned such as to be located in front of the patient's eyes, when in use. According to some embodiments, the light detectors 730a and 730b may be configured to detect the light exiting the patient's pupils as a result of the light emitted by light sources 720a/514 and 720b/514, as essentially described herein. According to some embodiments, the light detectors 730a and 730b may include one or more image capturing device, such as a camera, configured to capture one or more images and/or videos of the light exiting the patient's pupils as a result of the light emitted by light sources. According to some embodiments, the device 510/700 may be configured for emitting, transmitting and/or detecting light from either the right or left eye of the patient, or both. According to some embodiments, the device 510/700 may be configured for emitting light using the one or more inducing light sources, thereby stimulating the pupil, as described in greater detail elsewhere herein. According to some embodiments, the device 510/700 may be configured for emitting light in the visible range of wavelengths.

According to some embodiments, the hood 702a/702b may be configured to minimize photon escape from around the eye of the patient. According to some embodiments, the hood 702a/702b may be configured to minimize photon escape from the sides of the eye of the patient. According to some embodiments, the hood 702a/702b may include a base such as a plate positioned near the side and/or around the eye of the patient. According to some embodiments, the hood may extend along and/or between any one or more of the frame front 714 and the frame temples 712a and 712b. According to some embodiments, the hood 702a/702b may include a shoulder and/or flap configured to extend toward the skin of the user and/or abut thereto. According to some embodiments, at least a portion of an inner surface of the hood 702a/702b may include a reflective surface configured to redirect photons towards the vitreous cavity. According to some embodiments, the reflective surface may include a coating wherein the coating includes high light reflecting properties. According to some embodiments, the reflective surface and/or the reflective coating may include a smooth and/or polished material. According to some embodiments, the reflective surface and/or coating may include a metal composition. According to some embodiments, at least a portion of an inner surface of the hood 702a/702b may include a light absorbing material configured to absorb photons scattered back from the temple. According to some embodiments, the light absorbing surface may include a coating wherein the coating includes high light absorbing properties.

Figure 8:
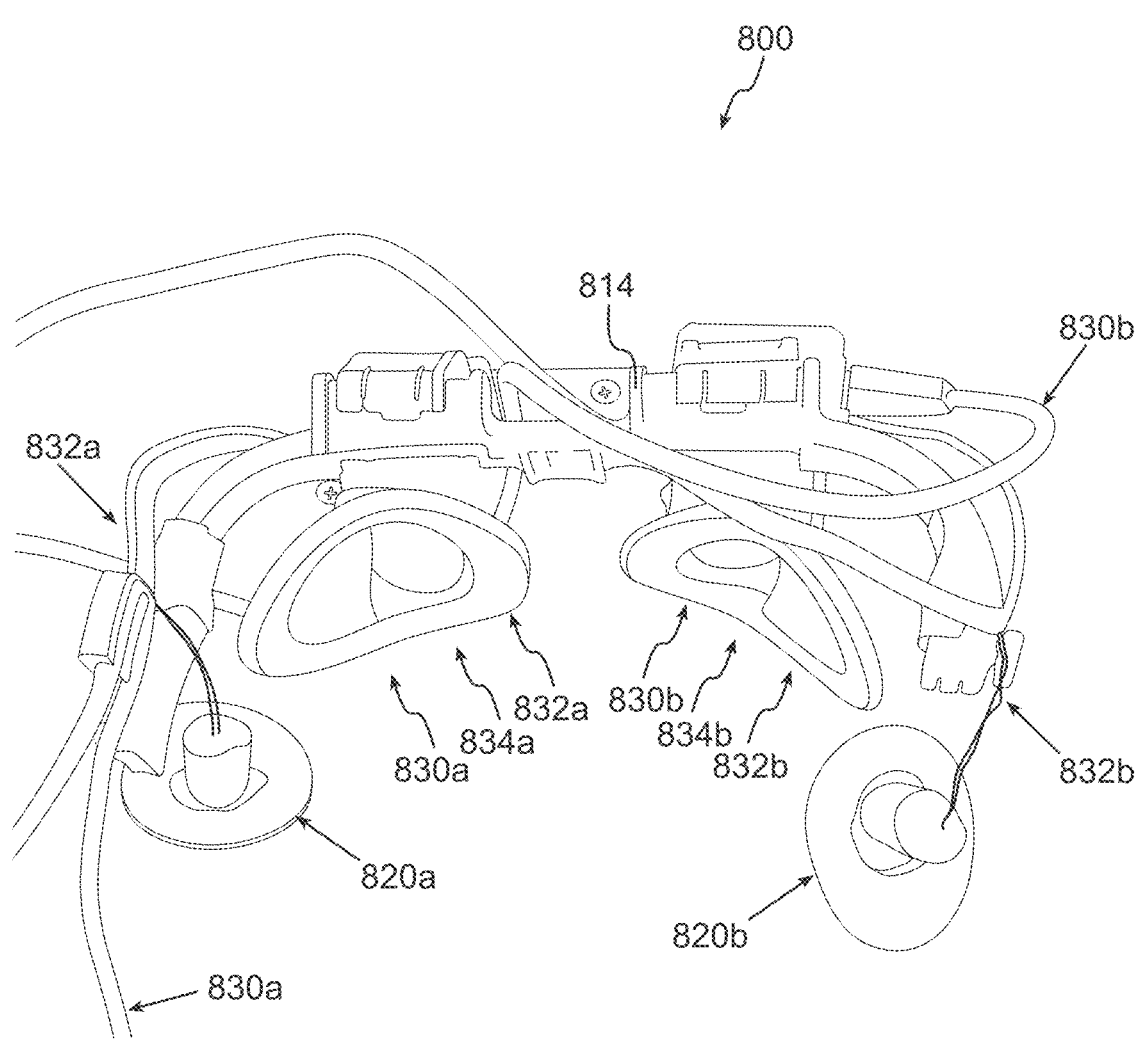

Reference is made to FIG. 8 which shows a schematic illustration of a device 800 for examining a pupil of a patient having closed eyelids, in accordance with some embodiments of the present disclosure.

According to some embodiments, the device 800 may be configured for examining a pupil of a patient having closed eyelids. According to some embodiments, the device 800 may be configured for determining a pupil size, pupil movement, pupil reactivity, and/or pupillary reflex of a patient having closed eyelids, and/or the change/percentage of the change of the pupil size relative to a baseline size thereof. According to some embodiments, the device 800 may be configured for determining a status of brain and/or nerve functions of a patient in an emergency setting or ambulance. Alternatively or additionally, the device 800 may be configured for monitoring pain levels and/or anesthesia or sedation levels of the patient based on the pupils examining.

According to some embodiments, the device 800 may include one or more light emitting assemblies 820a/820b, configured to emit light toward a vitreous cavity of the patient through a temple of the patient, such as described in greater detail elsewhere herein. According to some embodiments, the light emitting assemblies 820a and 820b may be identical, similar or different from the one or more light sources 720a/720b. According to some embodiments, essentially all light emitted from the one or more light emitting assemblies 820*a*/820*b* is configured to enter the temple of the patient.

According to some embodiments, the device 800 may include a platform unit used for wearing by the patient, such as a frame front 814. According to some embodiments, the frame front 814 advantageously allows positioning and retaining the device 800 on a patient having a limited access to the eyes and/or head, e.g., due to presence of medical equipment, bandages, injuries, and the like, or any combination thereof.

According to some embodiments, the front frame 814 may be adjustable. As a non-limiting example, the front frame 814 may include hinges adjustable to the distance between the eyes of the patient. According to some embodiments, the front frame 814 may be made of polymeric materials. According to some embodiments, the frame front 814 may be manufactured by 3D printing.

According to some embodiments, the front frame 814 may include flexible materials and/or a flexible mechanism, to facilitate positioning and/or adjusting the device 800. According to some embodiments, the front frame 814 may include flexible materials and/or a flexible mechanism to facilitate associating the front frame 814 with additional components/features, as described in greater detail elsewhere herein.

According to some embodiments, the frame front 814 may be associated with a band/strap (not shown) to facilitate fixing the position thereof. Alternatively, in some embodiments no additional fixing means are associated with the frame front 814.

According to some embodiments, the frame front 814 is associated with housings 832*a* and 832*b*. According to some embodiments, the housings 832*a* and 832*b* may be in a form of eyecups, i.e., rim curved vessels configured to fit the orbit of the eye.

According to some embodiments, the housings 832*a* and 832*b* may be made of a material essentially impermeable to light.

According to some embodiments, each of the housings 832*a* and 832*b* includes each of openings 834*a* and 834*b* configured for passage of the emitted light. According to some embodiments, each of the housings 832*a* and 832*b* includes each of light detectors 830*a* and 830*b*. According to some embodiments, the light detectors 830*a* and 830*b* configured to detect the light exiting the patient's pupils as a result of the light emitted by the one or more light emitting assemblies 820*a* and 820*b*.

According to some embodiments, the light detectors 830*a* and 830*b* may include one or more image capturing devices, such as a camera, configured to capture one or more images and/or videos of the light exiting the patient's pupils as a result of the light emitted by one or more light emitting assemblies 820*a* and 820*b*, through a closed eyelid of the patient.

According to some embodiments, the housings 832*a* and 832*b* may be detachably associated or integrally formed with the frame front 814. According to some embodiments, the orientation of the housings 832*a* and 832*b* may be tailored/adjusted to facilitate positioning thereof in front of the patient's eyes, when in use. According to some embodiments, each of the housings 832*a* and 832*b* may be independently associated with the front frame 814. According to some embodiments, the position and/or orientation of each of the housings 832*a* and 832*b* may be independently adjusted. As a non-limiting example, the position and orientation of the one or more image capturing devices may be independently adjusted by the flexible mechanism of the front frame 814, minimizing/preventing the effect of each of the one or more image capturing devices (e.g., the effect, in operation, of a first image capturing device on a second image capturing device). Alternatively or additionally, each of the housings 832*a* and 832*b* may include a maneuverable connection, such as but not limited to, flexible mechanism, joint, hook, fold, hinge, and the like, or any combination thereof, to facilitate independent retaining, positioning, adjusting thereof to the front frame 814.

According to some embodiments, the device 800 may be in communication with a system for examining a pupil of a patient, such as the disclosed herein systems 500 and/or 600. According to some embodiments, the communication may be wireless. Alternatively or additionally, the communication may be wired. As a non-limiting example and as depicted in FIG. 8, the one or more light emitting assemblies 820*a* and 820*b* may be in communication with a system for examining a pupil of a patient via wires 832*a* and 832*b*, respectively. As a non-limiting example and as depicted in FIG. 8, the light detectors 830*a* and 830*b* may be in communication with a system for examining a pupil of a patient via wires 830*a* and 830*b*, respectively.

According to some embodiments, the device 800 may be in a communication with at least one hardware processor, and/or with a non-transitory computer-readable storage medium having stored thereon a program code. According to some embodiments, a program code executable by the at least one hardware processor to: receive a plurality of consecutive frames of the pupil of the patient, identify the pupil of the patient by analyzing an intensity of the light transmitted through the eyelid as captured in the plurality of consecutive frames, track the location of the identified pupil of the patient in at least a portion of the plurality of consecutive frames, and determine a status of brain and/or nerve functions of the patient is based, at least in part, on the tracked location of the identified pupil of the patient.

Figure 9:
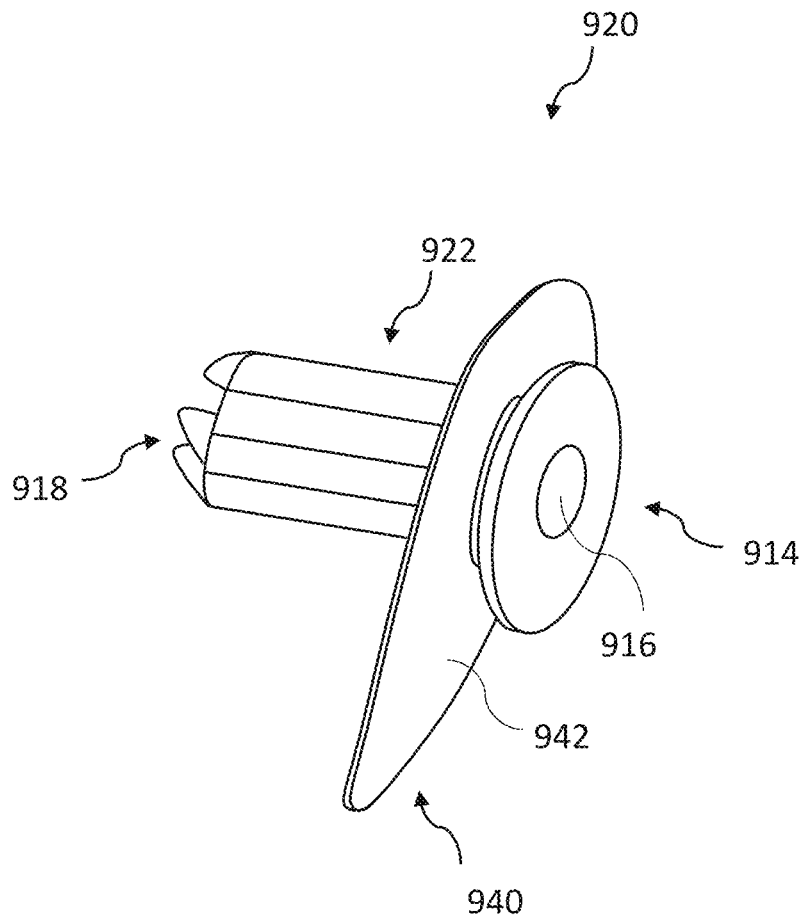

Alternatively or additionally, the platform unit may include one or more temple/side frames (e.g., frame temples 712*a* and 712*b* depicted in FIG. 7). According to some embodiments, each of the housings 832*a* and 832*b* may be detachably associated or integrally formed with the one or more temple/side frames, thereby reducing the weight and/or size of the platform unit positioned in front of the eyes of the patient. Put differently, in some embodiments, the platform unit of device 800 may not include a front frame (e.g., the front frame 814). In some embodiments, the weight and/or size the device 800 may be further reduced by associating the one or more image capturing devices and/or the light detectors with the patient (i.e., without associating thereof with a front or temple/side frame). As a non-limiting example, the one or more image capturing devices and/or the light detectors may be connected and/or associated by using electrical wires, i.e., without using additional means such as housing, front frame, temple/side frame, and the like. Reference is made to FIG. 9 which shows a schematic illustration of a perspective side view of a light emitting assembly 920, according to some embodiments.

According to some embodiments, the light emitting assembly 920 may be identical, similar or different from the light emitting assemblies 820*a*/820*b*.

According to some embodiments, the light emitting assembly 920 is configured to transmit light through a skin of the patient and into a cavity of a body organ/tissue of the patient. According to some embodiments, the light emitting assembly 920 may be positioned on outer body part of the patient (e.g., skin surface, bandage/medical dressing, and the like or any combination thereof) and is configured to illuminate therethrough an internal body tissue/organ of the patient. According to some embodiments, the light emitting assembly 920 advantageously allows examining a pupil of a patient having closed eyelids. According to some embodiments, the light emitting assembly 920 is configured to transmit light through the temples of the subject towards the pupils of the patient.

According to some embodiments, the light emitting assembly 920 includes a housing 922 having an outer layer and an inner layer. According to some embodiments, the housing 922 configured to retain one or more light sources 914 in the inner layer thereof.

According to some embodiments, the one or more light sources 914 may include a matrix of light sources (i.e. two or more light sources). According to some embodiments, the matrix of light sources may include light sources illuminating at identical, similar or different wavelengths. As a non-limiting example, a light emitting assembly including a set of two light emitting assemblies, wherein each of the two light emitting assemblies is configured to emit light towards each of the eyes of a patient, each of the two light emitting assemblies may include a matrix of light sources illuminating each of the eyes with the same or different wavelengths.

According to some embodiments, the housing may include a surface essentially transparent to light emitted from the one or more light sources 914. According to some embodiments, the housing may include essentially a transparent surface configured to transmit the light emitted by the one or more light source 914.

According to some embodiments, the housing may include an opening 916 configured to allow transmittance of light emitted from the one or more light sources 914.

According to some embodiments, the housing 922 may be permanently or detachably associated with an additional device, e.g., a device for examining a pupil of a patient. As a non-limiting example, the housing 922 may be detachably associated with the frame front 814 of the device 800 for examining a pupil of a patient. According to some embodiments, the detachable association may include, among others, a quick-locking mechanism, such as a snap fit mechanism (not shown).

According to some embodiments, the light emitting assembly 920 is compatible with any one of the disclosed systems and devices, such as but not limited to the system 600. According to some embodiments, the light emitting assembly 920 may be in a communication with a device and/or a system for examining a pupil of a patient and/or an image capturing device (e.g., the image capturing device 512). According to some embodiments, the light emitting assembly 920 may be in a communication with a storage medium (e.g., the storage medium 504), and/or a processing module (e.g., the processing module 502). According to some embodiments, the communication may include wireless communications. Alternatively or additionally, the communication may include wired communications. According to some embodiments, the housing 922 may include an opening/slot 918 allowing a wired connection therethrough.

According to some embodiments, the one or more light sources 914 configured to transmit light into an internal body part of the subject. According to some embodiments, the light assembly 920 may include two light emitting assemblies 920, wherein each of the two light emitting assemblies 920 includes one or more light sources 914 e.g., a first light emitting assembly having a first light source configured to emit light towards the right vitreous cavity from the right temple of the patient, and a second light emitting device having a second light source configured to emit light towards the left vitreous cavity from the left temple of the patient.

According to some embodiments, the light emitting assembly 920 may include more than two light sources 914 such as 3, 4, 5 or more light sources. Each possibility is a separate embodiment.

According to some embodiments, the one or more light sources 914 may be configured to emit light within the spectrum of near Infra-Red (IR) range, such as, about 750 nm to about 1500 nm. According to some embodiments, the one or more light sources 914 may be configured to emit light within the range of 400-750 nm, 650-1500 nm, 750-1400 nm, 750-1200 nm, 750-1000 nm, 800-1000 nm or any other suitable range. Each possibility is a separate embodiment. According to some embodiments, the one or more light sources 914 may be configured to emit light at a wavelength and/or intensity, which does not affect the pupils' diameter. According to some embodiments, the one or more light sources 914 may be configured to emit light at a wavelength and/or intensity enabling its transmission through the patient's head to the vitreous cavity without heating or causing damage to surrounding tissue.

According to some embodiments, the one or more light sources 914 may be an LED. According to some embodiments, the one or more light sources 914 may be a laser. According to some embodiments, the one or more light sources 914 may be a lamp. According to some embodiments, the one or more light sources 914 may be a single light source. According to some embodiments, the single light source may be capable of emitting light reaching the vitreous cavity of both the patient's eyes, either simultaneously or consecutively (for example due to movement of the light source relative to the patient's eyes).

According to some embodiments, the one or more light sources 914 may be an inductive light source, (i.e., a light source transmitting light having a wavelength and/or intensity, which induces a pupillary reflex as described in greater detail elsewhere herein). According to some embodiments, the device and/or the one or more light sources may further include an inductive light source configured to emit inductive light (light capable of inducing a pupillary reflex), i.e., in the range of 400-700 nm. The visible light is configured to be emitted towards the patient's eye(s), through the closed eyelid(s) and is configured to induce the pupillary reflex.

According to some embodiments, the light emitting assembly 920 includes a contact pad 940. According to some embodiments, the contact pad 940 may be integrally formed with the housing. Alternatively, the contact pad 940 may be detachably attached to an outer layer of the housing 922.

According to some embodiments, the contact pad 940 is configured to be attached to the temples of the user. According to some embodiments, the contact pad 940 may include different shapes, such as but not limited to, circular, D-shaped, elliptical, square, rectangular, triangular, polygonal, and/or polygon-like, or any combination thereof.

According to some embodiments, the contact pad 940 may be attached directly to the skin of the user. According to some embodiments, the contact pad 940 may be attached indirectly, e.g., on a bandage, gauze, pad, compress, medical dressing, and the like. Scenarios wherein it may be beneficial to mount the light emitting assembly 920 indirectly on the subject may include, among others, injuries such as head injury, post-surgery conditions, and the like, without scraping and/or exposing the skin or otherwise impeding the recovery of the subject.

According to some embodiments, the contact pad 940 includes or made of natural and/or synthetic polymers. According to some embodiments, the contact pad 940 may include a foam, fabric, tape, and the like. According to some embodiments, the contact pad 940 includes an adhesive surface 942. According to some embodiments, the adhesive surface 942 may include a surface, coating, and/or layer (collectively referred to as "adhesive surface"). According to some embodiments, the adhesive surface 942 may be made of biocompatible materials. According to some embodiments, the adhesive surface 942 includes or made of adhesion gel, glue, adhesive tape, and the like, configured to attach/mount the light emitting assembly 920 to the patient, e.g., to the temples of the patient.

Alternatively or additionally, the contact pad 940 may include micro-protrusions, such as needles, pins, tips, to facilitate fixing/retaining the light emitting assembly 920, directly or indirectly, to the subject.

According to some embodiments, the housing 922 may include or be in a form of a snap/clip and the like, to facilitate attaching and/or allow fastening, directly or indirectly, to the patient and/or to a device for examining a pupil of a patient (e.g., the device 800).

According to some embodiments, the light emitting assembly 920 may be disposable. According to some embodiments, the light emitting assembly 920 is configured for a single use for a single subject. According to some embodiments, the light emitting assembly 920 may be used in a single session and be placed at a plurality of sites. According to some embodiments, the light emitting assembly 920 may be at least partially disposable, i.e., include disposable and reusable components. As a non-limiting example, the contact pad 940 may be disposable, while the housing 922 may be reusable.

EXAMPLES

Example 1

The pupillary response of twelve subjects was measured by three different techniques—using commonly applied methods in the art, a pupillometer and a penlight, and one of the disclosed herein methods (referred to as "BrainWatch"). A comparison of the experimental results of the disclosed BrainWatch method with the pupilometer and with penlight method are depicted in FIGS. 10A and 10B, respectively. FIG. 10C shows a comparison of the pupillary reactivity of the penlight with the pupilometer method. FIG. 11 shows a plot of the pupil reactivity of dilated and normal-sized eyes obtained by the disclosed BrainWatch methods and by the pupilometer method; The experimental results of the average pupillary reactivity are summarized and presented in FIG. 12. According to FIGS. 11 and 12, it is evident that the pupillary reactivity measured by the "BrainWatch" method is similar compared to the values measured by the commonly applied methods pupilometer and penlight. As shown in FIG. 11, the pupillary reactivity both of normal sized pupils and of dilated pupils determined by the BrainWatch methods correspond to the values obtained by the pupilometer. However, in contrast to the pupilometer and penlight, which are designed for manual measurement of open eyelids, the "BrainWatch" method measured the pupillary reactivity while the eyelids of the subjects are closed. Further, in contrast to the pupilometer and the penlight methods, the BrainWatch methods advantageously allow human-independent examination of the pupils of the patient, i.e., without a caregiver, nurse, and the like. Hence, in some embodiments, the disclosed BrainWatch methods may be implemented for examining the pupils of the subject in an emergency setting, e.g., during a surgery, wherein the eyes of the patient are closed (often using a plaster) for minimizing drying thereof. According to some embodiments, the disclosed BrainWatch methods may advantageously notify the medical staff regarding the pupillary activity and/or the brain and/or nerve functions of the patient in real time, without interfering the medical procedure. Scenarios for which it might be particularly beneficial to utilize the BrainWatch method and/or the BrainWatch index includes those requiring an immediate medical intervention to promote patient survival and a positive neurological outcome.

It should be noted that the light intensity emitted from the eyes of the subjects may vary across the eye, e.g., due to the positioning of the light sources on the temples of the subject. For example, as the pupil gets closer to the outer side of the eye, the illumination the signal that comes out of the pupil becomes stronger. The varying light intensity emitted from the pupils of the subject may complicate the disclosed pupil examination process and thus be misinterpreted as a change in pupil size. This may be particularly evident when the examined subject has frequent and/or rapid pupil movement. Advantageously, as evident from FIGS. 10-12, the herein disclosed BrainWatch methods obtained reliable results when examining the pupils of the subjects.

Example 2

A closed right eye of a patient suffering from a brain injury was examined by the disclosed herein "BrainWatch" method. Videos of the pupils of the patient having closed eye lids were recorded using the disclosed methods, under near infra-red (NIR) illumination. The video recording sequence duration was 14 seconds, both eyes of the patient were simultaneously recorded. The video data was recorded separately for each of the eyes. During the recording sequence, visual light was used for activation each of the eyes, first the right eye (at about 1.8 seconds) and a few seconds later (at about 8.2 seconds) the left eye of the patient. Data obtained from each of the eyes was analyzed by applying machine learning techniques and algorithms. The algorithm included analysis of the obtained videos frame by frame for determining/detecting the pupil center. A grey level threshold (TH) was defined for searching and identifying a valid pupil and its center by searching and finding a blob of light that best fits the defined requirements of the pupil. It should be noted that several THs may be used for optimizing the search of a valid option of the pupil. The valid option depends on several morphological requirements, such as the shape of the pupil (e.g., conformity to circularity), the size of the pupil (e.g., above a certain minimal size), and, optionally, the location of the pupil, and/or the location of the pupil relative to previous frames thereof. Once a pupil center location is found/identified, a search window centered around the pupil center location is defined and positioned around the pupil center location.

The algorithm includes calculating the average sum of grey level ($GL_n$) in the search window for each of the frames of the video according to formula (1):

$$GL_n = \frac{\text{Total Sum of } GL \text{ in Search Window}}{\text{Number of pixels in Search Window}} \tag{1}$$

The algorithms includes defining a pupil size baseline according to the average grey level values of the pupil (e.g., when the pupil is at a large state), according to formula (2):

$$\text{Baseline} = \text{Average } (GL_{n=0-t1 \; sec}) \qquad (2)$$

The algorithm may optionally include normalizing the data according to the pupil size baseline, according to formula (3):

$$\text{Normalized } GL_n = \frac{GL_n}{\text{baseline}} \qquad (3)$$

The normalizing may be optionally performed for comparing and/or analyzing data obtained from different sources and/or by using different features/components, such as but not limits to, different patients and/or different video parameters.

The algorithm includes determining the minimum grey level values for the right and the left eyes after visible lights are turned on, according to formulas (4) and (5):

$$\text{Min}_R = \text{minimum } (NGL_{n=t1-t2 \; sec}) \qquad (4)$$

$$\text{Min}_L = \text{minimum } (NGL_{n=t3-tend \; sec}) \qquad (5)$$

The algorithms includes calculating the pupillary reactivity for light, including direct and consensual, according to formulas (6) and (7):

$$R_R = \frac{\text{Baseline} - \text{Min}_R}{\text{Baseline}} \qquad (6)$$

$$R_L = \frac{\text{Baseline} - \text{Min}_L}{\text{Baseline}} \qquad (7)$$

The results are depicted in FIG. 13, which shows the reactivity as a function of time. As shown in FIG. 11, a patient-specific baseline of a pupil reactivity is obtained, such that a reactivity value of about 100% corresponds to a pupil size when essentially no light enters therein. FIG. 11 further shows that at about 1.8 seconds the right eye of the patient was illuminated, leading to rapidly decreased reactivity, indicating constriction of the right pupil (i.e. direct pupil response). At about 8.2 seconds a left eye of the patient was illuminated, resulting in rapidly decreasing reactivity of the right eye, hence indicating constriction of the right pupil (i.e. consensual pupillary light reflex). According to some embodiments, the ability to calculate and analyze direct and consensual pupil responses is of great importance, allowing determining a status of brain and/or nerve functions of the patient, such as but not limited to, bleeding, nerve response, edema, and the like, or any combination thereof.

Unless otherwise defined the various embodiment of the present invention may be provided to an end user in a plurality of formats, platforms, and may be outputted to at least one of a computer readable memory, a computer display device, a printout, a computer on a network, a tablet or a smartphone application or a user. Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software (or program code), selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "processor" "hardware processor" or "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a PDA (personal data assistant), a pager. Any two or more of such devices in communication with each other, and/or any computer in communication with any other computer, may optionally comprise a "computer network".

Embodiments of the present invention may include apparatuses for performing the operations herein. This apparatus may be specially constructed for the desired purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EE-PROMs), magnetic or optical cards, or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

In the description and claims of the application, the words "include" and "have", and forms thereof, are not limited to members in a list with which the words may be associated.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods according to some embodiments may be described in a specific sequence, methods of the disclosure may include some or all of the described stages carried out in a different order. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A method for determining a status of brain and/or nerve functions of a patient, the method comprising:

obtaining a plurality of consecutive frames capturing light transmitted through a closed eyelid of the patient;

identifying the pupil of the patient in real time by analyzing an intensity of the light transmitted through the eyelid as captured in the plurality of consecutive frames;

tracking the location of the identified pupil of the patient in real time in at least a portion of the plurality of consecutive frames, wherein tracking the location comprises determining a frequency and/or a degree of movement of the pupil of the patient by tracking a change in coordinates of pixels within a segment identified as being associated with the pupil of the patient; and determining a status of brain and/or nerve functions of the patient based, at least in part, on the degree of movement of the identified pupil, wherein determining the status comprises determining whether the status of brain and/or nerve functions is normal or abnormal.

2. The method of claim 1, further comprising emitting light toward a vitreous cavity of the patient using one or more light sources and wherein the light captured in the plurality of consecutive frames is the light emitted by the one or more light sources.

3. The method of claim 1, further comprising contouring at least one segment having a plurality of pixels with a high gray level in at least one frame within the plurality of consecutive frames wherein the high gray level comprises a value of gray level above a predetermined maximum threshold.

4. The method of claim 3, further comprising determining a shape of the at least one segment, and wherein identifying of the pupil of the patient is based, at least in part, on the shape of the at least one segment.

5. The method of claim 3, further comprising determining a gray level distribution and/or a maximal gray level value within the at least one segment, and wherein identifying of the pupil of the patient is based, at least in part, on the gray level distribution within the at least one segment.

6. The method of claim 3, further comprising identifying at least one segment having a plurality of pixels with a high gray level within each of at least two frames within the plurality of consecutive frames and comparing between at least two identified segments associated with different frames within the plurality of consecutive frames, wherein identifying of the pupil of the patient is based, at least in part, on the comparison between the at least two identified segments.

7. The method of claim 6, wherein comparing between the at least two identified segments comprises comparing any one or more of the shape and/or gray level distribution of the segments and/or a change in gray level within the segments.

8. The method of claim 6, wherein comparing between the at least two identified segments comprises comparing the coordinates of pixels within the segment and/or the coordinates of the shape and/or gray level distribution of pixels within the segments.

9. The method of claim 1, further comprising mapping the intensity of the light transmitted through the eyelid of the patient.

10. The method of claim 1, further comprising determining a baseline pupil size of the pupil of the patient, wherein the baseline pupil size comprises at least one of a large baseline size and/or a small baseline size of the pupil of the patient.

11. The method of claim 10, wherein the determining the status of brain and/or nerve functions of the patient is further based on the baseline pupil size and/or on change in size of the pupil as a function of time.

12. The method of claim 1, further comprising classifying the status of the brain and/or nerve functions of the patient as normal or abnormal, based, at least in part, on the size of the pupil of the patient and/or on the change in the size of the pupil of the patient as a function of time.

13. The method of claim 3, further comprising contouring at least one segment having a plurality of pixels with a high gray level in at least one frame within the plurality of consecutive frames and determining a shape of the at least one segment, and identifying the pupil of the patient based, at least in part, on the shape of the at least one segment.

14. The method of claim 13, further comprising identifying at least one segment having a plurality of pixels with a high gray level within each of at least two frames within the plurality of consecutive frames and comparing between at least two identified segments associated with different frames within the plurality of consecutive frames, and identifying the pupil of the patient based, at least in part, on the comparison between the at least two identified segments.

15. The method of claim 14, wherein comparing between the at least two identified segments comprises comparing one or more of: any one or more of the shape and/or gray level distribution of the segments, a change in gray level within the segments, the coordinates of pixels within the segment and/or coordinates of the shape and/or gray level distribution of pixels within the segments.

16. The method of claim 13, further comprising identifying one of the at least one segment as being associated with a pupil of the patient.

17. A system for examining a pupil of a patient, comprising:

at least one hardware processor in communication with at least one image capturing device configured to capture a plurality of consecutive frames of a pupil of a patient through a closed eyelid of the patient;

a non-transitory computer-readable storage medium having stored thereon program code, the program code executable by the at least one hardware processor to:

receive the plurality of consecutive frames of the pupil of the patient;

identify, for pixels within the plurality of consecutive frames, a minimal gray level value throughout the plurality of consecutive frames;

generate a minimal gray level frame based, at least in part, on the identified minimal gray level values of the pixels;

subtract the gray level values of pixels within the minimal gray level frame from gray level values of corresponding pixels within the rest of the frames of the plurality of consecutive frames, thereby generating a processed plurality of consecutive frames;

locate the pupil of the patient within at least one frame of the processed plurality of consecutive frames;

calculate the size of the pupil of the patient;

track a location of the identified pupil in real time in at least a portion of the plurality of consecutive frames, wherein tracking the location comprises determining a frequency and/or a degree of movement of the pupil by tracking a change in coordinates of the pixels within a segment identified as being associated with the pupil; and determine a status of brain and/or nerve functions of the patient based, at least in part, on the calculated size of the pupil of the patient, wherein determining the status comprises determining whether the status of brain and/or nerve functions is normal or abnormal.

\* \* \* \* \*